(12) United States Patent
Jung et al.

(10) Patent No.: US 8,277,724 B2
(45) Date of Patent: *Oct. 2, 2012

(54) STERILIZATION METHODS AND SYSTEMS

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1050 days.

This patent is subject to a terminal disclaimer.

(21) Appl. No.: 11/396,256

(22) Filed: Mar. 31, 2006

(65) Prior Publication Data

US 2007/0231189 A1    Oct. 4, 2007

(51) Int. Cl.
| *A61L 2/24* | (2006.01) |
| *A61L 2/00* | (2006.01) |
| *A61L 2/04* | (2006.01) |
| *A61L 9/00* | (2006.01) |
| *A61L 11/00* | (2006.01) |
| *C23F 11/00* | (2006.01) |

(52) U.S. Cl. .............. 422/3; 422/1; 422/22; 422/24
(58) Field of Classification Search .............. 422/1, 3, 422/22, 24
See application file for complete search history.

(56) References Cited

U.S. PATENT DOCUMENTS

| 2,216,333 | A | 10/1940 | White et al. |
| 2,689,837 | A | 9/1954 | Darby et al. |
| 2,873,263 | A | 2/1959 | Lal |
| 2,875,097 | A | 2/1959 | Pritchard |
| 2,986,448 | A | 5/1961 | Gates et al. |
| 3,325,436 | A | 6/1967 | Prindle et al. |
| 3,376,110 | A | 4/1968 | Shiraeff |
| 3,376,384 | A | 4/1968 | Achramowicz |
| 3,480,557 | A | 11/1969 | Shiraeff |
| 3,485,787 | A | 12/1969 | Haefele et al. |
| 3,827,999 | A | 8/1974 | Crossland |

(Continued)

FOREIGN PATENT DOCUMENTS

EP    0693289 A2    1/1996

(Continued)

OTHER PUBLICATIONS

Advanced Sterilization Products; "Frequently Asked Questions"; pp. 1-3; located at http://www.sterrad.com/products_&_services/sterrad/sterrad_nx/faqs/index.asp; bearing a date of 2006; printed on Mar. 3, 2006.

(Continued)

*Primary Examiner* — Regina M. Yoo
(74) *Attorney, Agent, or Firm* — Suiter Swantz pc llo

(57) ABSTRACT

Methods and systems for sterilizing one or more areas or one or more portions of one or more areas are described. In some embodiments, the methods and systems can be used to sterilize one or more areas or one or more portions of one or more areas through use of sterilizing radiation. In some embodiments, the methods and systems can be utilized so that objects, such as humans, that are within one or more areas or one or more portions of one or more areas are not substantially irradiated with sterilizing radiation.

12 Claims, 25 Drawing Sheets

U.S. PATENT DOCUMENTS

| | | | |
|---|---|---|---|
| 3,870,783 A | 3/1975 | Hall et al. | |
| 3,953,566 A | 4/1976 | Gore | |
| 3,966,902 A | 6/1976 | Chromecek | |
| 3,967,478 A | 7/1976 | Guinn | |
| 4,042,765 A | 8/1977 | Floyd et al. | |
| 4,073,764 A | 2/1978 | Hemmerich et al. | |
| 4,087,925 A | 5/1978 | Bienek | |
| 4,151,419 A | 4/1979 | Morris et al. | |
| 4,169,123 A | 9/1979 | Moore et al. | |
| 4,169,124 A | 9/1979 | Forstrom et al. | |
| 4,176,240 A | 11/1979 | Sabia | |
| 4,187,390 A | 2/1980 | Gore | |
| 4,194,041 A | 3/1980 | Gore et al. | |
| 4,197,375 A | 4/1980 | Fox | |
| 4,208,324 A | 6/1980 | Ramanathan | |
| 4,312,907 A | 1/1982 | Hiraoka et al. | |
| 4,325,870 A | 4/1982 | Bühler et al. | |
| 4,369,284 A | 1/1983 | Chen | |
| 4,381,380 A | 4/1983 | LeVeen et al. | |
| 4,403,826 A | 9/1983 | Presby | |
| 4,443,511 A | 4/1984 | Worden et al. | |
| 4,476,255 A | 10/1984 | Bailey et al. | |
| 4,499,154 A | 2/1985 | James et al. | |
| 4,500,455 A | 2/1985 | Niwa et al. | |
| 4,556,464 A | 12/1985 | St. Clair | |
| 4,612,444 A | 9/1986 | Ragusa | |
| 4,618,213 A | 10/1986 | Chen | |
| 4,629,896 A | 12/1986 | Bridgen | |
| 4,642,165 A | 2/1987 | Bier | |
| 4,643,876 A | 2/1987 | Jacobs et al. | |
| 4,688,585 A | 8/1987 | Vetter | |
| 4,692,369 A | 9/1987 | Nomi | |
| 4,716,183 A | 12/1987 | Gamarra et al. | |
| 4,731,541 A | 3/1988 | Shoemaker | |
| 4,744,951 A | 5/1988 | Cummings et al. | |
| 4,771,482 A | 9/1988 | Shlenker | |
| 4,774,324 A | 9/1988 | Loeffler et al. | |
| 4,855,412 A | 8/1989 | Dehnert et al. | |
| 4,855,413 A | 8/1989 | Dehnert et al. | |
| 4,907,316 A | 3/1990 | Kurz | |
| 4,925,732 A | 5/1990 | Driskill et al. | |
| 4,935,260 A | 6/1990 | Shlenker | |
| 4,935,635 A | 6/1990 | O'Harra | |
| 4,942,270 A | 7/1990 | Gamarra | |
| 4,943,414 A | 7/1990 | Jacobs et al. | |
| 5,008,093 A | 4/1991 | Merianos | |
| 5,008,106 A | 4/1991 | Merianos et al. | |
| 5,030,380 A | 7/1991 | Moschner et al. | |
| 5,061,106 A | 10/1991 | Kent | |
| 5,069,227 A | 12/1991 | Maronian | |
| 5,074,322 A | 12/1991 | Jaw | |
| 5,077,047 A | 12/1991 | Biss et al. | |
| 5,102,711 A | 4/1992 | Keller et al. | |
| 5,113,874 A | 5/1992 | Maronian | |
| 5,138,719 A | 8/1992 | Orlianges et al. | |
| 5,142,010 A | 8/1992 | Olstein | |
| 5,269,981 A | 12/1993 | Jameson et al. | |
| 5,315,289 A * | 5/1994 | Fuller et al. | 340/532 |
| 5,326,841 A | 7/1994 | Fellman | |
| 5,357,636 A | 10/1994 | Dresdner, Jr. et al. | |
| 5,360,892 A | 11/1994 | Bonsignore et al. | |
| 5,403,363 A | 4/1995 | Loeffler et al. | |
| 5,428,123 A | 6/1995 | Ward et al. | |
| 5,459,879 A | 10/1995 | Fuchs | |
| 5,480,915 A | 1/1996 | Burns | |
| 5,498,394 A | 3/1996 | Matschke | |
| 5,501,669 A | 3/1996 | Conway et al. | |
| 5,547,635 A | 8/1996 | Duthie, Jr. | |
| 5,549,924 A | 8/1996 | Shlenker et al. | |
| 5,557,444 A | 9/1996 | Melville et al. | |
| 5,563,238 A | 10/1996 | Bonsignore et al. | |
| 5,614,151 A | 3/1997 | LeVay et al. | |
| 5,641,566 A | 6/1997 | Kranzler et al. | |
| H1670 H | 7/1997 | Aziz et al. | |
| 5,644,798 A | 7/1997 | Shah | |
| 5,648,003 A | 7/1997 | Liang et al. | |
| 5,667,753 A | 9/1997 | Jacobs et al. | |
| 5,688,475 A | 11/1997 | Duthie, Jr. | |
| 5,731,053 A | 3/1998 | Kuhn et al. | |
| 5,733,270 A | 3/1998 | Ling et al. | |
| 5,779,795 A | 7/1998 | Bucher et al. | |
| 5,783,290 A | 7/1998 | Isaac et al. | |
| 5,786,598 A | 7/1998 | Clark et al. | |
| 5,788,925 A | 8/1998 | Pai et al. | |
| 5,788,940 A | 8/1998 | Cicha et al. | |
| 5,798,165 A | 8/1998 | Mizoguchi et al. | |
| 5,851,551 A | 12/1998 | Tseng et al. | |
| 5,901,564 A | 5/1999 | Comeau, II | |
| 5,920,075 A | 7/1999 | Whitehead | |
| 5,945,068 A | 8/1999 | Ferone | |
| 5,948,707 A | 9/1999 | Crawley et al. | |
| 5,959,423 A | 9/1999 | Nakanishi et al. | |
| 5,965,276 A | 10/1999 | Shlenker et al. | |
| 6,010,727 A | 1/2000 | Rosenthal | |
| 6,038,331 A | 3/2000 | Johnson | |
| 6,132,784 A * | 10/2000 | Brandt et al. | 426/248 |
| 6,177,677 B1 | 1/2001 | Alboresi et al. | |
| 6,192,887 B1 | 2/2001 | Howett et al. | |
| 6,193,931 B1 | 2/2001 | Lin et al. | |
| 6,223,137 B1 | 4/2001 | MaCay et al. | |
| 6,252,128 B1 | 6/2001 | Obata | |
| 6,254,625 B1 | 7/2001 | Rosenthal et al. | |
| 6,311,974 B1 | 11/2001 | Koga | |
| 6,326,654 B1 | 12/2001 | Ruden et al. | |
| 6,335,529 B1 | 1/2002 | Sekii et al. | |
| 6,343,425 B1 | 2/2002 | Sias et al. | |
| 6,370,694 B1 | 4/2002 | Michelson | |
| 6,426,701 B1 | 7/2002 | Levy et al. | |
| 6,429,438 B1 | 8/2002 | Smestad | |
| 6,459,955 B1 | 10/2002 | Bartsch et al. | |
| 6,485,979 B1 | 11/2002 | Kippenhan et al. | |
| 6,490,351 B1 | 12/2002 | Roberts | |
| 6,521,552 B1 | 2/2003 | Honna et al. | |
| 6,524,698 B1 | 2/2003 | Schmoock | |
| 6,530,498 B1 | 3/2003 | Ovadia | |
| 6,560,782 B2 | 5/2003 | Hourihan et al. | |
| 6,573,836 B1 | 6/2003 | Gitis et al. | |
| 6,577,240 B2 | 6/2003 | Armstrong | |
| 6,610,254 B1 | 8/2003 | Furner et al. | |
| 6,656,424 B1 | 12/2003 | Deal | |
| 6,663,805 B1 | 12/2003 | Ekiner et al. | |
| 6,676,871 B1 | 1/2004 | Benassi et al. | |
| 6,706,243 B1 | 3/2004 | Sias et al. | |
| 6,716,352 B1 | 4/2004 | Livingston | |
| 6,727,818 B1 | 4/2004 | Wildman et al. | |
| 6,733,495 B1 | 5/2004 | Bek et al. | |
| 6,755,536 B2 | 6/2004 | Tegreene et al. | |
| 6,765,029 B2 | 7/2004 | Arakawa et al. | |
| 6,806,361 B1 | 10/2004 | Kajisa et al. | |
| 6,872,366 B2 | 3/2005 | Thomas et al. | |
| 6,882,278 B2 | 4/2005 | Winings et al. | |
| 6,901,712 B2 | 6/2005 | Lionel | |
| 6,913,758 B2 | 7/2005 | Hourihan et al. | |
| 6,925,679 B2 | 8/2005 | Wallach et al. | |
| 6,937,221 B2 | 8/2005 | Lippert et al. | |
| 6,949,222 B1 | 9/2005 | Möller et al. | |
| 6,961,541 B2 | 11/2005 | Overy et al. | |
| 6,963,289 B2 | 11/2005 | Aljadeff et al. | |
| 6,968,194 B2 | 11/2005 | Aljadeff et al. | |
| 6,991,761 B2 | 1/2006 | Hehenberger et al. | |
| 7,009,185 B2 | 3/2006 | Chi et al. | |
| 7,015,816 B2 | 3/2006 | Wildman et al. | |
| 7,056,971 B2 | 6/2006 | Varma | |
| 7,101,408 B2 | 9/2006 | Himeno et al. | |
| 7,104,519 B2 | 9/2006 | O'Maley et al. | |
| 7,122,150 B2 | 10/2006 | Gonzalez et al. | |
| 7,149,531 B2 | 12/2006 | Misikangas | |
| 7,175,807 B1 * | 2/2007 | Jones | 422/24 |
| 7,196,662 B2 | 3/2007 | Misikangas et al. | |
| 7,209,752 B2 | 4/2007 | Myllymäki et al. | |
| 7,228,136 B2 | 6/2007 | Myllymäki et al. | |
| 7,286,057 B2 | 10/2007 | Bolling | |
| 7,295,115 B2 | 11/2007 | Aljadeff et al. | |
| 7,299,059 B2 | 11/2007 | Misikangas et al. | |
| 7,349,683 B2 | 3/2008 | Misikangas et al. | |
| 7,403,108 B2 | 7/2008 | Aljadeff et al. | |
| 7,408,470 B2 | 8/2008 | Wildman et al. | |

| | | | | | | |
|---|---|---|---|---|---|---|
| 7,482,936 | B2 | 1/2009 | Bolling | EP | 1 609 488 A1 | 12/2005 |
| 7,522,049 | B2 | 4/2009 | Aljadeff et al. | EP | 2 180 334 A3 | 10/2011 |
| 7,616,122 | B2 | 11/2009 | Bolling | GB | 2291350 A | 1/1996 |
| 7,616,124 | B2 | 11/2009 | Paessel et al. | JP | 1139139 | 5/1989 |
| 7,729,707 | B2 | 6/2010 | Aljadeff et al. | JP | 07289616 A | 11/1995 |
| 7,904,097 | B2 | 3/2011 | Misikangas | JP | 08071132 A | 3/1996 |
| 7,936,275 | B2 | 5/2011 | Bolling | JP | 08071133 A | 3/1996 |
| 7,982,619 | B2 | 7/2011 | Bolling | JP | 08215110 | 8/1996 |
| 8,020,733 | B2 | 9/2011 | Snodgrass | JP | 2000220334 | 8/2000 |
| 8,056,768 | B2 | 11/2011 | Snodgrass | JP | 2002364055 | 12/2002 |
| 8,208,939 | B2 | 6/2012 | Aljadeff et al. | JP | 2003250865 | 9/2003 |
| 2002/0011934 | A1 | 1/2002 | Cacioli et al. | JP | 2004317512 | 11/2004 |
| 2002/0085947 | A1* | 7/2002 | Deal ............................. 422/24 | WO | WO 95/17634 | 6/1995 |
| 2002/0158814 | A1 | 10/2002 | Bright et al. | WO | WO 01/10476 A1 | 2/2001 |
| 2002/0175182 | A1 | 11/2002 | Matthews | WO | WO 01/60419 | 8/2001 |
| 2002/0192340 | A1 | 12/2002 | Swart et al. | WO | WO 01/60419 A1 | 8/2001 |
| 2003/0030562 | A1 | 2/2003 | Lane et al. | WO | WO 03/056951 A2 | 7/2003 |
| 2003/0081293 | A1 | 5/2003 | Wood, Jr. et al. | WO | WO 2004/032019 A2 | 4/2004 |
| 2003/0093503 | A1 | 5/2003 | Yamaki et al. | WO | WO 2004/035095 A1 | 4/2004 |
| 2003/0145664 | A1 | 8/2003 | Schwarz et al. | WO | WO2004/080494 A1 | 9/2004 |
| 2003/0164285 | A1 | 9/2003 | Korenev | WO | WO2004080494 | 9/2004 |
| 2003/0170901 | A1 | 9/2003 | Kippenhan et al. | WO | WO 2005/048041 A2 | 5/2005 |
| 2003/0194344 | A1 | 10/2003 | Brafford et al. | WO | WO2005/077076 A2 | 8/2005 |
| 2003/0235605 | A1 | 12/2003 | Lelah et al. | WO | WO2005077076 | 8/2005 |
| 2004/0024290 | A1 | 2/2004 | Root et al. | WO | WO 2006/007729 A1 | 1/2006 |
| 2004/0056201 | A1 | 3/2004 | Fink et al. | WO | WO 2010/059678 A2 | 5/2010 |
| 2004/0072577 | A1 | 4/2004 | Myllymaki et al. | WO | WO 2011/033504 A1 | 3/2011 |
| 2004/0090333 | A1 | 5/2004 | Wildman et al. | WO | WO 2011/058228 A1 | 5/2011 |
| 2004/0139555 | A1 | 7/2004 | Conrad et al. | | | |
| 2004/0176108 | A1 | 9/2004 | Misikangas | | | |
| 2004/0203870 | A1 | 10/2004 | Aljadeff et al. | | | |
| 2004/0211444 | A1 | 10/2004 | Taylor et al. | | | |
| 2004/0244138 | A1 | 12/2004 | Taylor et al. | | | |
| 2005/0013729 | A1 | 1/2005 | Brown-Skrobot et al. | | | |
| 2005/0022844 | A1 | 2/2005 | Field et al. | | | |
| 2005/0069453 | A1 | 3/2005 | Forng et al. | | | |
| 2005/0128139 | A1 | 6/2005 | Misikangas et al. | | | |
| 2005/0131635 | A1 | 6/2005 | Myllymaki et al. | | | |
| 2005/0135965 | A1 | 6/2005 | Williams et al. | | | |
| 2005/0136944 | A1 | 6/2005 | Misikangas et al. | | | |
| 2005/0156711 | A1 | 7/2005 | Aljadeff et al. | | | |
| 2005/0181804 | A1 | 8/2005 | Misikangas et al. | | | |
| 2005/0186108 | A1* | 8/2005 | Fields ............................. 422/4 | | | |
| 2005/0197139 | A1 | 9/2005 | Misikangas et al. | | | |
| 2005/0207381 | A1 | 9/2005 | Aljadeff et al. | | | |
| 2005/0214506 | A1 | 9/2005 | Lee et al. | | | |
| 2005/0236579 | A1 | 10/2005 | Jenkins et al. | | | |
| 2005/0249791 | A1 | 11/2005 | Hobbs et al. | | | |
| 2005/0267233 | A1* | 12/2005 | Joshi ............................. 523/122 | | | |
| 2006/0071799 | A1 | 4/2006 | Verdiramo | | | |
| 2006/0216193 | A1 | 9/2006 | Johnson et al. | | | |
| 2006/0236496 | A1 | 10/2006 | Oh et al. | | | |
| 2007/0008149 | A1 | 1/2007 | Bolling | | | |
| 2007/0046460 | A1 | 3/2007 | Aljadeff et al. | | | |
| 2007/0103296 | A1 | 5/2007 | Paessel et al. | | | |
| 2007/0117568 | A1 | 5/2007 | Misikangas et al. | | | |
| 2007/0149215 | A1 | 6/2007 | Misikangas | | | |
| 2008/0037512 | A1 | 2/2008 | Aljadeff et al. | | | |
| 2008/0184518 | A1 | 8/2008 | Taylor et al. | | | |
| 2008/0186231 | A1 | 8/2008 | Aljadeff et al. | | | |
| 2008/0283786 | A1 | 11/2008 | Snodgrass | | | |
| 2009/0166382 | A1 | 7/2009 | Snodgrass | | | |
| 2009/0266842 | A1 | 10/2009 | Snodgrass | | | |
| 2009/0273465 | A1 | 11/2009 | Shamir et al. | | | |
| 2010/0117823 | A1 | 5/2010 | Wholtjen | | | |
| 2010/0123560 | A1 | 5/2010 | Nix et al. | | | |
| 2010/0262430 | A1 | 10/2010 | Gips et al. | | | |
| 2010/0308076 | A1 | 12/2010 | Snodgrass | | | |
| 2011/0018769 | A1 | 1/2011 | Misikangas et al. | | | |
| 2011/0050501 | A1 | 3/2011 | Aljadeff | | | |
| 2011/0063106 | A1 | 3/2011 | Snodgrass | | | |
| 2011/0163870 | A1 | 7/2011 | Snodgrass | | | |
| 2011/0195701 | A1 | 8/2011 | Cook et al. | | | |
| 2011/0227740 | A1 | 9/2011 | Wohltjen | | | |
| 2011/0291841 | A1 | 12/2011 | Hollock et al. | | | |

FOREIGN PATENT DOCUMENTS

| | | | |
|---|---|---|---|
| EP | 1 537 796 A2 | 6/2005 | |
| EP | 1 609 488 A | 12/2005 | |

OTHER PUBLICATIONS

Big Sky Laser; "Nd:YAG & Dye Laboratory Lasers from Quantel"; pp. 1-6; located at http://www.bigskylaser.com/lablasers.html#td1190; printed on Mar. 22, 2006.

Big Sky Laser; "The Brilliant Series of Nd:YAG Laser oscillators and accessories"; p. 1; located at http://www.bigskylaser.com/brilliantseries.html; printed on Mar. 22, 2006.

Enhance-It; "Mobile Room Sterilizers"; p. 1; located at http://www.enhance-it.com/06mobile.htm; bearing a date of 1999-2006; printed on Mar. 22, 2006.

Enhance-It; "Portable Germicidal Units"; p. 1; located at http://www.enhance-it.com/05portable.htm; bearing a date of 1999-2006; printed on Mar. 22, 2006.

Enhance-It; "Ultraviolet Light"; p. 1-2; located at http://www.enhance-it.com/uaprod.htm; bearing a date of 1999-2006; printed on Mar. 22, 2006.

Globalspec; "About UV Light Systems"; pp. 1-3; located at http://light-sources.globalspec.com/LearnMore/Optics_Optical_Components/Light_Sources/Process_UV_Lamps_Systems; bearing a date of 1999-2006; printed on Mar. 22, 2006.

Hilton, Paul; "Nd:YAG laser welding"; TWI World Centre for Materials Joining Technology; pp. 1-2; located at http://www.twi.co.uk/j32k/protected/band_3/kspah003.html; bearing a date of 2001; printed on Mar. 22, 2006.

Medical Device Link; "Equipment News: Packaging and Sterilization Equipment—Machine Designers Address Space, Validation Issues"; Medical Product Manufacturing News; pp. 1-5; located at http://www.devicelink.com/mpmn/archive/01/04/004.html; bearing a date of Apr. 2001; printed on Mar. 22, 2006.

Wikipedia; "Nd:YAG laser"; pp. 1-2; located at http://en.wikipedia.org/wiki/Nd-YAG_laser; bearing a date of Feb. 23, 2006; printed on Mar. 22, 2006.

Xenon Corporation; "SteriPulse-XL-Sterilization and Decontamination Systems"; pp. 1-6; located at http://www.xenoncorp.com/sterilization.html; printed on Mar. 23, 2006.

Creative Concepts; "Creative Oz-Air (i) Pvt. Ltd: Ozone Ambient Air Monitor & Controller, Hands Sterilizer, U.V. Systems, Ozone Test Kits, Ozone Accessories"; pp. 1-3; Creative Oz-Air (i) Pvt. Ltd.; located at http://www.creativeconceptsozair.com/ozoneambient.html#handstenlizer; printed on Apr. 25, 2006.

De Kock, Servaas; "Marketplace: Ozone Dry hand Sterilizing Unit"; pp. 1-2; located at http://www.ecademy.com/module.php?mod=list&lid=11053; bearing a date of Dec. 3, 2005; Ecademy; Cape Town, South Africa; printed on Apr. 25, 2006.

Elgan, Mike; "The Raw Feed Archives: Unexpected Convergence: Mouse and Hand Sterilizer"; pp. 1-6; located at http://www.mikeslist.com/2003_09_28_archive.html; bearing a date of Oct. 4, 2003; Mike's List; printed on Apr. 25, 2006.

Enhance-It; "Portable Germicidal Units", p. 1, located at http://www.enhance-it.com/04portable.htm, bearing a date of 1999-2006; Enhance-It, LLC; printed on Mar. 22, 2006.

HRS; "Specialty/Hygiene System—Hand Sterilizer"pp. 1-2; located at http://www.hrs.co.kr/english/hrs_specialty_hand.htm; bearing a date of 2004; HRS, Seoul, South Korea; printed on Apr. 25, 2006.

Marhoc; "Marhoc's Automatic Hand Sterilizer U.S. Patent #-6,872,366" pp. 1-3; located at http://www.marhoc.com/Marhoc_Hand_Sterilizer.htm; bearing a date of 2005; Marhoc, printed on Apr. 25, 2006.

Nehmzow, U.; "Mobile Robotics: A Practical Introduction," $2^{nd}$ Edition, 2003, ISBN No. 1852337265, Springer, London, UK (not provided).

Olgear; "Ozone Dry Hand Sterilising unit"; pp. 1-2; located at http://www.olgear.com/sites/58/images/ozone_hand_steriliser.pdf.

Siegwart, Roland; Nourbakhsh, Illah R.; "Introduction to Autonomous Mobile Robots," 2004, ISBN No. 0-262-19502-X, The MIT Press, Cumberland, RI (not provided).

Tidybio; "No-touch fully inductive control: Quick-speed and efficient sterilization: No need of water supply and quick-speed air-drying: Easy Operation without waste"; pp. 1-7; located at http://www.tidybio.cn/english/Sterilizer.shtml; bearing a date of 2003-2005; Beijing Tidybio Science & Technology Co., Ltd., printed on Apr. 25, 2006.

Xie, Ming; "Fundamentals of Robotics: Linking Perception to Action," 2003, ISBN No. 9812383131, World Scientific Publishing Co. Pte. Ltd., River Edge, NJ (not provided).

U.S. Appl. No. 11/442,688, filed May 26, 2006, Jung et al.
U.S. Appl. No. 11/442,699, filed May 26, 2006, Jung et al.
U.S. Appl. No. 11/440,460, filed May 23, 2006, Jung et al.
U.S. Appl. No. 11/414,743, filed Apr. 28, 2006, Jung et al.
U.S. Appl. No. 11/411,207, filed Apr. 25, 2006, Hyde et al.
U.S. Appl. No. 11/593,193, Jung et al.
U.S. Appl. No. 11/592,010, Ishikawa et al.
U.S. Appl. No. 11/584,435, Jung et al.
U.S. Appl. No. 11/584,339, Hyde et al.

"CDC Urges Hospitals to Tackle Drug-Resistant Infections"; The Wall Street Journal; bearing a date of Oct. 19, 2006; pp. 1-2; printed on Oct. 31, 2006.

Smith, Ann; Heckelman, Patricia E.; O'Neil, Maryadele J. (Ed); Budavari, Susan (Ed); The Merck Index: An Encyclopedia of Chemicals, Drugs and Biologicals; bearing a date of Oct. 2001; 2564 pages; $13^{th}$ Edition; ISBN No. 0911910131; John Wiley and Sons and Merck & Co. Inc.; Whitehouse Station, NJ (not provided).

Smith, Michael; "ICAAC: Rhinovirus on Hands Blocked by Solution for Hours"; MedPage Today; Bearing dates of Oct. 2, 2006 and 2004-2006; pp. 1-2; San Francisco; MedPage Today, LLC; printed on Oct. 19, 2006.

U.S. Appl. No. 11/891,357, Jung et al.

PCT International Search Report; International App. No. PCT/US 07/23129; Apr. 10, 2008; pp. 1-2.

PCT International Search Report; International App. No. PCT/US 07/07582; Apr. 11, 2008; pp. 1-2.

PCT International Search Report; International App. No. PCT/US 07/07846, Nov. 18, 2008, pp. 1-2.

PCT International Search Report; International App. No. PCT/US07/07673, Oct. 10, 2008, pp. 1-2.

PCT International Search Report; International App. No. PCT/US07/07845, Sep. 18, 2008, pp. 1-2.

U.S. Appl. No. 60/605,066, filed Aug. 27, 2004, Taylor, Charles E.

European Search Report; European App. No. EP 07 75 4150; Sep. 14, 2009; pp. 1-6.

U.S. Appl. No. 12/800,814, Hyde et al.

State Intellectual Property Office of P.R.C.; Application No. 200780040949.2; Jul. 16, 2010; pp. 1-7.

UK Intellectual Property Office Examination Report Under Section 18(3); App. No. GB0908938.4; Mar. 1, 2011 (received by our Agent on Mar. 3, 2011); pp. 1-5.

U.S. Appl. No. 12/384,168, Jung et al.
U.S. Appl. No. 12/384,166, Jung et al.
U.S. Appl. No. 12/587,143, Jung et al.
U.S. Appl. No. 12/587,142, Jung et al.
U.S. Appl. No. 12/587,104, Hyde et al.

Supplementary European Search Report; European App. No.: 07774171.8; Sep. 14, 2009; 6 Total Pages.

Supplementary European Search Report; European App. No.: 07754226.4; Sep. 14, 2009; 7 Total Pages.

Supplementary European Search Report; European App. No.: 07754375.9; Sep. 14, 2009; 6 Total Pages.

Supplementary European Search Report; European App. No.: 07754150.6; Sep. 14, 2009; 6 Total Pages.

State Intellectual Property Office of P.R.C.; Notification of the First Office Action; App. No. 2007/80040949.2 (PCT/US07/023129); Jul. 16, 2010 (received by our Agent on Mar. 19, 2012); pp. 1-5.

Rospierski, Jeffrey; "Actuator for Fluid Dispenser"; United States Design Patent; Patent No. D654,743 S; Date of Patent Feb. 28, 2012; 7 Total Pages.

* cited by examiner

STERILIZATION METHODS AND SYSTEMS

TECHNICAL FIELD

The present disclosure relates to methods and systems that may be used in many contexts such as sterilization of healthcare related areas.

SUMMARY

In some embodiments, a sterilization method is provided that includes determining if one or more objects are present or absent within one or more areas and transmitting one or more signals to one or more sources of sterilizing radiation in response to the determining. In addition to the foregoing, other method aspects are described in the claims, drawings, and/or text forming a part of the present application.

In some embodiments, a sterilization method is provided that includes approximating one or more distances from one or more sources of sterilizing radiation to one or more surfaces within one or more areas and transmitting one or more signals to the one or more sources of sterilizing radiation in response to the approximating. In addition to the foregoing, other method aspects are described in the claims, drawings, and/or text forming a part of the present application.

In some embodiments, a sterilization method is provided that includes receiving one or more signals from one or more detectors and emitting sterilizing radiation in response to the receiving. In addition to the foregoing, other method aspects are described in the claims, drawings, and/or text forming a part of the present application.

In some embodiments, a sterilization system is provided that includes means for determining if one or more objects are present or absent within one or more areas and means for transmitting one or more signals to one or more sources of sterilizing radiation responsive to the means for determining if one or more objects are present or absent within one or more areas.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

In some embodiments, a sterilization system is provided that includes circuitry for determining if one or more objects are present or absent within one or more areas and circuitry for transmitting one or more signals to one or more sources of sterilizing radiation responsive to the circuitry for determining if one or more objects are present or absent within one or more areas. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings and the following claims and detailed description.

DETAILED DESCRIPTION

Figure 1A:
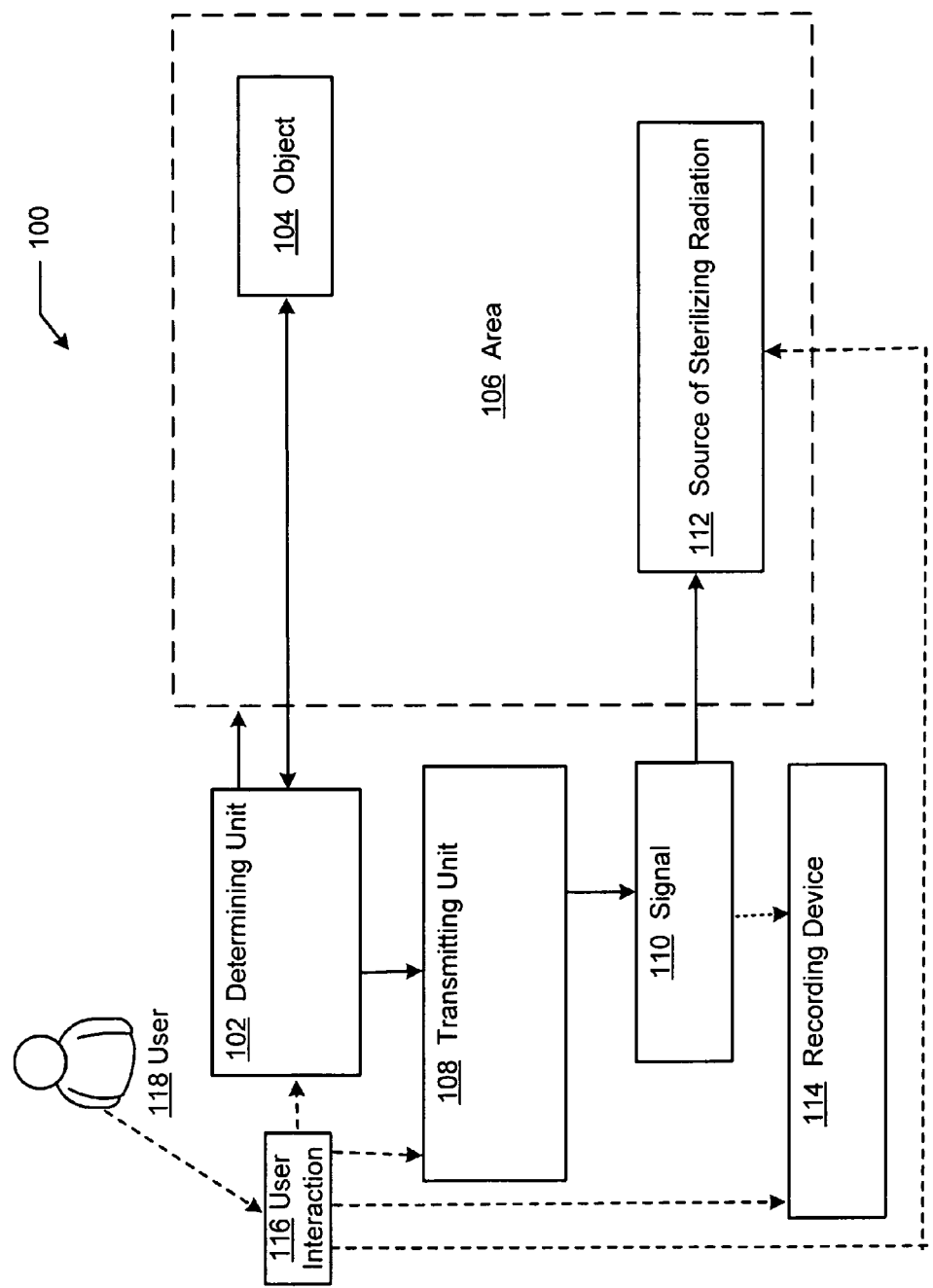
FIG. 1A illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1A illustrates an example system 100 in which embodiments may be implemented. In some embodiments, the system 100 is operable to provide a sterilization method that may be used to sterilize one or more areas, one or more portions of one or more areas, one or more objects within an area, and/or substantially any combination thereof. In some embodiments, the system 100 is operable to provide a sterilization method that can be used to sterilize one or more areas, sterilize one or more portions of one or more areas, sterilize one or more objects within one or more areas, avoid sterilizing one or more areas, avoid sterilizing one or more portions of one or more areas, avoid sterilizing one or more objects within one or more areas, and/or substantially any combination thereof. In some embodiments, the system 100 is operable to sterilize one or more areas or one or more portions of one or more areas without exposing one or more humans present within the one or more areas or one or more portions of the one or more areas to sterilizing radiation. In some embodiments, the system 100 is operable to sterilize one or more areas or one or more portions of one or more areas without substantially exposing one or more humans present within the one or more areas or one or more portions of the one or more areas to sterilizing radiation.

The system 100 includes one or more determining units 102. The one or more determining units can be used to determine if one or more objects 104 are present or absent within one or more areas or portions of one or more areas 106. In some embodiments, the one or more determining units 102 can detect one or more signals associated with one or more humans. In some embodiments, the one or more determining units 102 can determine one or more distances between surfaces within the one or more areas 106. In some embodiments, the one or more determining units 102 can determine if one or more shadows are present within one or more areas 106. In some embodiments, the one or more determining units 102 can determine one or more shapes that correspond to one or more objects present or absent within one or more areas 106. The one or more determining units 102 may utilize numerous technologies. For example, a determining unit 102 can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; computer modeling; range finders, such as laser and infrared range finders; and/or substantially any combination thereof.

The system 100 includes the presence or absence of one or more objects 104. Numerous objects may be present or absent within one or more areas or one or more portions of one or more areas. Examples of such objects include, but are not limited to, humans, non-human animals, plants, surgical instruments, cooking utensils, eating utensils, sinks, tables, machinery, waste areas, and the like.

The system 100 includes one or more areas or one or more portions of one or more areas 106. The system 100 may be used within numerous areas and portions of areas. Examples of such areas include, but are not limited to, hospitals, such as operating rooms and wards; transportation, such as airplanes, trains, cars, subways, buses; kitchens; bathrooms; and the like. In some embodiments, one or more areas can include portions of one or more areas. Examples of portions of one or more areas include, but are not limited to, one or more sinks within one or more operating rooms, one or more tables within one or more operating rooms, one or more sections of flooring within one or more operating rooms, one or more sections of siding within one or more operating rooms, and the like. The one or more areas or one or more portions of one or more areas 106 can contain numerous types of contamination. Examples of such contamination can include, but are not limited to, bacteria, fungus, viruses, spores, microbes, eggs, and the like. Accordingly, sterilizing radiation can be used to kill or inactivate such contamination. Example irradiation parameters are provided in Table I and can be readily determined through standard protocols.

TABLE I

Sample Parameters for Sterilization with Ultraviolet Purifiers

| Bacteria | Energy in mW-sec/ $cm^2$ Sterilization up to 90% | Energy in mW-sec/ $cm^2$ Sterilization up to 99% |
|---|---|---|
| Bacillus anthracis | 4.52 | 9.04 |
| S. enteritidis | 4.00 | 8.00 |
| B. megatherium sp. (vegetative) | 1.30 | 2.60 |
| B. megatherium sp. (spores) | 2.73 | 5.46 |
| B. paratyphosus | 3.20 | 6.40 |
| B. subtilis | 7.10 | 14.20 |
| B. subtilis spores | 12.00 | 24.00 |
| Corynebacterium diphtheriae | 3.37 | 6.74 |
| Eberthella typhosa | 2.14 | 4.28 |
| Escherichia coli | 3.00 | 6.00 |
| Micrococcus candidus | 6.05 | 12.10 |
| Micrococcus sphaeroides | 10.00 | 20.00 |
| Neisseria catarrhalis | 4.40 | 8.80 |
| Phytomonas tumefaciens. | 4.40 | 8.80 |
| Proteus vulgaris | 2.64 | 5.28 |
| Pseudomonas aeruginosa | 5.50 | 11.00 |
| Pseudomonas fluorescens | 3.50 | 7.00 |
| S. typhimurium | 8.00 | 16.00 |
| Sarcina Lutea | 19.70 | 39.40 |
| Seratia marcescens | 2.42 | 4.84 |
| Dysentery bacilli | 2.20 | 4.40 |
| Shigella paradysenteriae | 1.68 | 3.36 |
| Spirillum rubrum | 4.40 | 8.80 |
| Staphylococcus albus | 1.84 | 3.68 |
| Staphylococcus aureus | 2.60 | 5.20 |
| Streptococcus hemolyticus | 2.16 | 4.32 |
| Streptococcus lactis | 6.15 | 12.30 |
| Streptocuccus viridans | 2.00 | 4.00 |

The system 100 includes one or more transmitting units 108. The one or more transmitting units 108 can transmit one or more signals 110 to one or more sources of sterilizing radiation 112 in response to one or more determining units 102. The one or more transmitting units 108 can transmit numerous types of signals 110 to one or more sources of sterilizing radiation 112. For example, the one or more transmitting units 108 can transmit a signal 110 that includes, but is not limited to, a hardwired signal, an infrared signal, an optical signal, a radiofrequency (RF) signal, a digital signal, an analog signal, or substantially any combination thereof to one or more sources of sterilizing radiation 112.

The system 100 includes one or more signals 110. The one or more signals 110 can include numerous types of information. In some embodiments, one or more signals 110 can include instructions for one or more sources of sterilizing radiation 112 to emit sterilizing radiation substantially constantly. In some embodiments, one or more signals 110 can include instructions for one or more sources of sterilizing radiation 112 to emit sterilizing radiation as a pulse. A signal 110 can include, but is not limited to, instructions with regard to numerous types and/or combinations of sterilizing radiation, such as ultraviolet light and/or gamma radiation, that are to be emitted from one or more sources of sterilizing radiation 112. In some embodiments, one or more signals 110 can include information related to wavelengths of radiation to be emitted from one or more sources of sterilizing radiation 112. For example, in some embodiments, one or more signals 110 can include instructions for one or more sources of sterilizing radiation 112 to emit ultraviolet light having wavelengths between 100 nanometers and 400 nanometers and/or substantially any combination of wavelengths between 100 nanometers and 400 nanometers. In other embodiments, one or more signals 110 can include instructions for one or more sources of sterilizing radiation 112 to emit ultraviolet light having wavelengths between 180 nanometers and 300 nanometers and/or substantially any combination of wavelengths between 180 nanometers and 300 nanometers. In other embodiments, one or more signals 110 can include instructions for one or more sources of sterilizing radiation 112 to emit ultraviolet light having wavelengths between 255 nanometers and 280 nanometers and/or substantially any combination of wavelengths between 255 nanometers and 280 nanometers. In other embodiments, one or more signals 110 can include instructions for one or more sources of sterilizing radiation 112 to emit ultraviolet light having wavelengths between 250 nanometers and 280 nanometers and/or substantially any combination of wavelengths between 250 nanometers and 280 nanometers. In still other embodiments, one or more signals 110 can include instructions for one or more sources of sterilizing radiation 112 to emit ultraviolet light having wavelengths that are centered, but asymmetric, and about 265 nanometers and/or substantially any combination of wavelengths of such light. In some embodiments, one or more signals 110 can include instructions for one or more sources of sterilizing radiation 112 to exclude the emission of one or more wavelengths of radiation from one or more sources of sterilizing radiation 112. One or more signals 110 can include instructions to direct the emission of sterilizing radiation from one or more sources of sterilizing radiation 112. One or more signals 110 can include instructions to shape the emission of sterilizing radiation from one or more sources of sterilizing radiation 112. One or more signals 110 can include instructions for one or more sources of sterilizing radiation 112 to emit numerous types of non-sterilizing radiation. Such non-sterilizing radiation can include, but is not limited to, infrared radiation, sonic radiation, ultrasonic radiation, and the like. In some embodiments, one or more signals 110 can include information related to distances between one or more surfaces within one or more areas 106 to one or more sources of sterilizing radiation 112. In some embodiments, such information can be used to direct sterilizing radiation. In some embodiments, such information can be used to shape and/or focus sterilizing radiation. In some embodiments, one or more signals 110 can be transmitted to one or more recording devices 114. In some embodiments, one or more signals 110 can include instructions for one or more sources of sterilizing radiation 112 to emit sterilizing radiation onto one or more areas 106 according to one or more sterilization levels assigned to the one or more areas 106. In some embodiments, one or more signals 110 can include instructions for one or more sources of sterilizing radiation 112 to emit sterilizing radiation onto one or more areas 106 in a prioritized manner. In some embodiments, one or more signals include instructions for one or more sources of sterilizing radiation to irradiate one or more areas 106 with respect to immediacy, latency, intensity, and the like. In some embodiments, a prioritized manner includes irradiating one or more areas 106 with regard to time-integrated intensity of sterilizing radiation such as irradiation of one or more areas 106 as functions of either relative or absolute locations in the reference enclosed volume so that high-patient-hazard or high-infectivity-likelihood areas and volumes can be specified for the most rigorous and/or frequent irradiation. One or more signals 110 can include instructions for one or more sources of sterilizing radiation 112 to emit sterilizing radiation in response to one or more shapes that correspond to one or more objects 104 within one or more areas 106.

The system 100 includes one or more sources of sterilizing radiation 112. Numerous sources of sterilizing radiation may be used within system 100. Examples of such sources of sterilizing radiation include, but are not limited to, emission from a cobalt-60 source, coherent light emitted from one or more frequency quadrupled-Nd YAG/glass lasers (neodymium-doped yttrium aluminum garnet (Nd:$Y_3Al_5O_{12}$), incoherent light emitted from one or more low-pressure mercury resonance lamps, emission from tunable dye lasers, and the like. Sources of sterilizing radiation are known in the art and are commercially available (XENON Corporation, Wilmington, Mass.; Big Sky Laser Technologies, Inc., Bozeman, Mont.; Enhance-It, LLC, Hilton Head Island, S.C. 29926 and Advanced Sterilization Products, Irvine, Calif. 92618). In some embodiments, one or more sources of sterilizing radiation 112 can emit one or more forms of non-sterilizing radiation. Examples of such non-sterilizing radiation include infrared radiation, sonic radiation, ultrasonic radiation, and the like. In some embodiments, one or more sources of sterilizing radiation 112 will emit sterilizing radiation according to parameters set at the one or more sources of sterilizing radiation 112. In some embodiments, one or more sources of sterilizing radiation 112 will emit sterilizing radiation according to instructions included within one or more signals 110 received by the one or more sources of sterilizing radiation 112. In some embodiments, one or more sources of sterilizing radiation 112 will emit sterilizing radiation according to parameters set at the one or more sources of sterilizing radiation 112 and according to instructions included within one or more signals 110 received by the one or more sources of sterilizing radiation 112. In some embodiments, emission of sterilizing radiation from one or more sources of sterilizing radiation can be started and stopped, intensity modulated, paused, initiated, interrupted, resumed, programmed to follow a preprogrammed schedule, routine or sequence, or substantially any combination thereof.

The system 100 may include one or more recording devices 114. In some embodiments, one or more signals 110 are transmitted to one or more recording devices 114. The one or more recording devices can record numerous types of information. In some embodiments, the one or more recording devices can record one or more frequencies of radiation, one or more intensities of radiation, one or more durations of irradiation, one or more wavelengths of radiation, one or more times of irradiation, one or more areas that were irradiated, the presence or absence of one or more objects within one or more areas, the identity of one or more objects present within one or more areas, the last time that one or more areas were irradiated, and/or substantially any combination thereof with which one or more areas were sterilized or partially sterilized. Many types of recording devices 114 may be used. Examples of such recording devices include, but are not limited to, many types of memory, optical disks, magnetic disks, magnetic tape, and the like. In some embodiments, one or more recording devices provide for user interaction 116.

The system 100 may provide for user interaction 116. In some embodiments, a user 118 may interact with one or more transmitting units 108, one or more determining units 102, one or more recording devices 114, one or more sources of sterilizing radiation 112, and/or substantially any combination thereof. Such interaction can include, but is not limited to, inputting instructions related to the sterilization of one or more areas or one or more portions of one or more areas with regard to time, place, duration, intensity, priority, and/or substantially any combination thereof. The user 118 can interact through use of numerous technologies. For example, user interaction 116 can occur through use of hardwired methods, such as through use of a keyboard, use of wireless methods, use of the internet, and the like.

In some embodiments, the sterilization method involves completely sterilizing one or more areas, partially sterilizing one or more areas, sterilizing a portion of one or more areas, sterilizing one or more objects within one or more areas, or substantially any combination thereof. In other embodiments, the method includes avoiding sterilization of one or more areas, avoiding sterilization of one or more portions of one or more areas, avoiding sterilization of one or more objects within one or more areas, or substantially any combination thereof. In still other embodiments, the method includes partially sterilizing one or more areas, sterilizing one or more portions of one or more areas, sterilizing one or more objects within one or more areas, avoiding sterilization of one or more areas, avoiding sterilization of one or more portions of one or more areas, avoiding sterilization of one or more objects within one or more areas, or substantially any combination thereof.

Figure 1B:
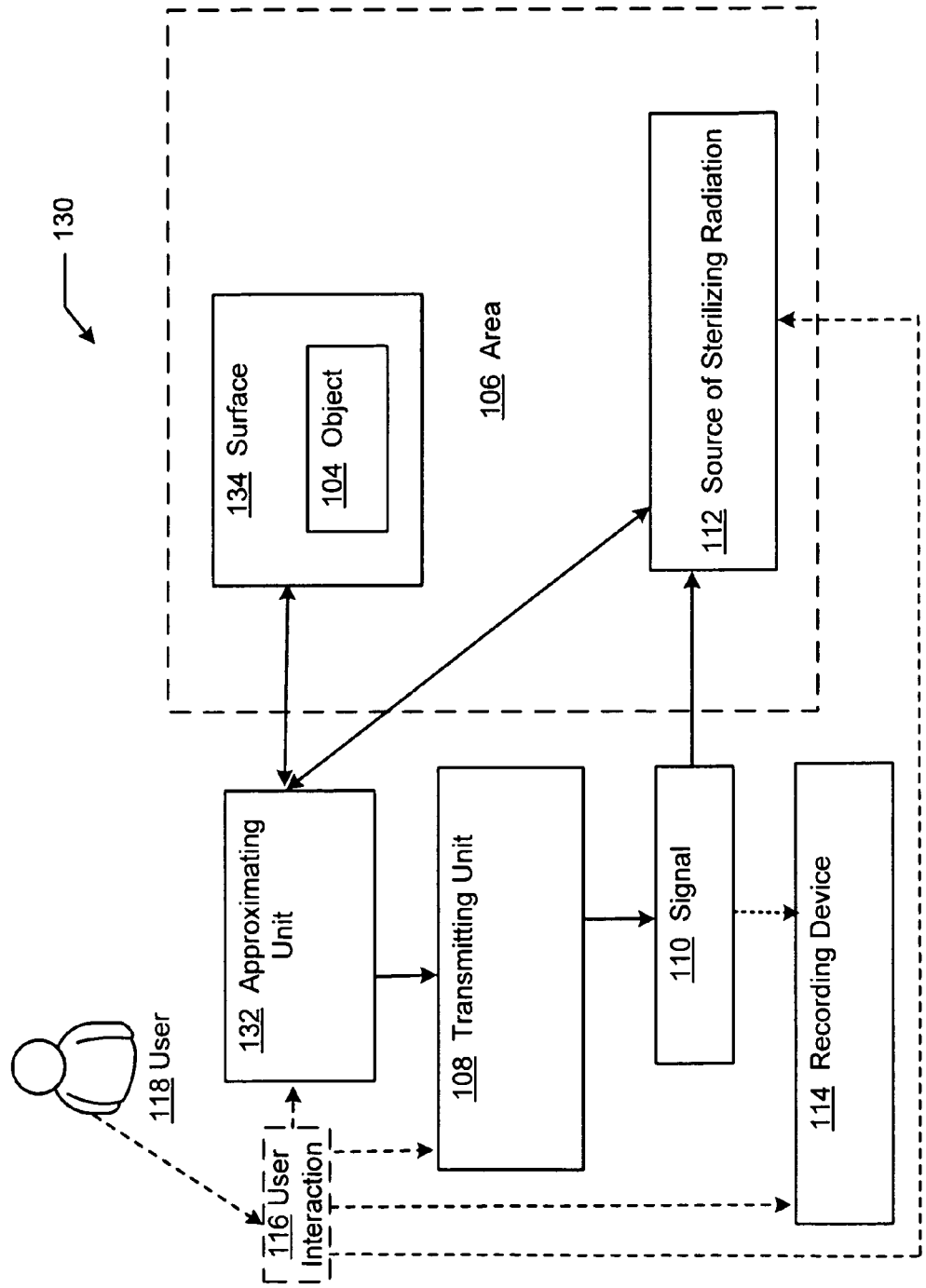
FIG. 1B illustrates an example system 130 in which embodiments may be implemented.

FIG. 1B illustrates an example system 130 in which embodiments may be implemented. In some embodiments, the system 130 is operable to provide a sterilization method that may be used to sterilize an area, a portion of an area, objects within an area, and/or substantially any combination thereof. In some embodiments, the system 130 is operable to provide a sterilization method that can be used to sterilize an area, sterilize a portion of an area, sterilize objects within an area, avoid sterilizing an area, avoid sterilizing a portion of an area, avoid sterilizing objects within an area, and/or substantially any combination thereof. In some embodiments, the system 130 is operable to sterilize an area or portion of an area 106 without exposing one or more humans present within the area or portion of the area 106 to sterilizing radiation. In some embodiments, the system 130 is operable to sterilize an area or portion of an area 106 without substantially exposing one or more humans present within the area or portion of the area 106 to sterilizing radiation.

The system 130 includes one or more approximating units 132. In some embodiments, the one or more approximating units 132 can be used to approximate one or more distances between one or more surfaces 134 within one or more areas 106. In some embodiments, the one or more approximating units 132 can be used to approximate one or more distances between one or more surfaces in one or more areas 106 and one or more sources of sterilizing radiation 112. In some embodiments, the one or more surfaces 134 are on one or more objects 104 included within the one or more areas 106. In some embodiments, the one or more surfaces 134 are on one or more humans. In some embodiments, the one or more approximating units 132 can approximate the distances between one or more shapes that correspond to one or more objects 104 present or absent within one or more areas 106. The one or more approximating units 132 may utilize numerous technologies. For example, an approximating unit 132 can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; computer modeling; range finders, such as laser and infrared range finders; and/or substantially any combination thereof. The approximated distances can be used to direct sterilizing radiation onto or away from one or more objects 104 or surfaces 134.

The other components of system 130 have been described with reference to system 100.

Figure 1C:
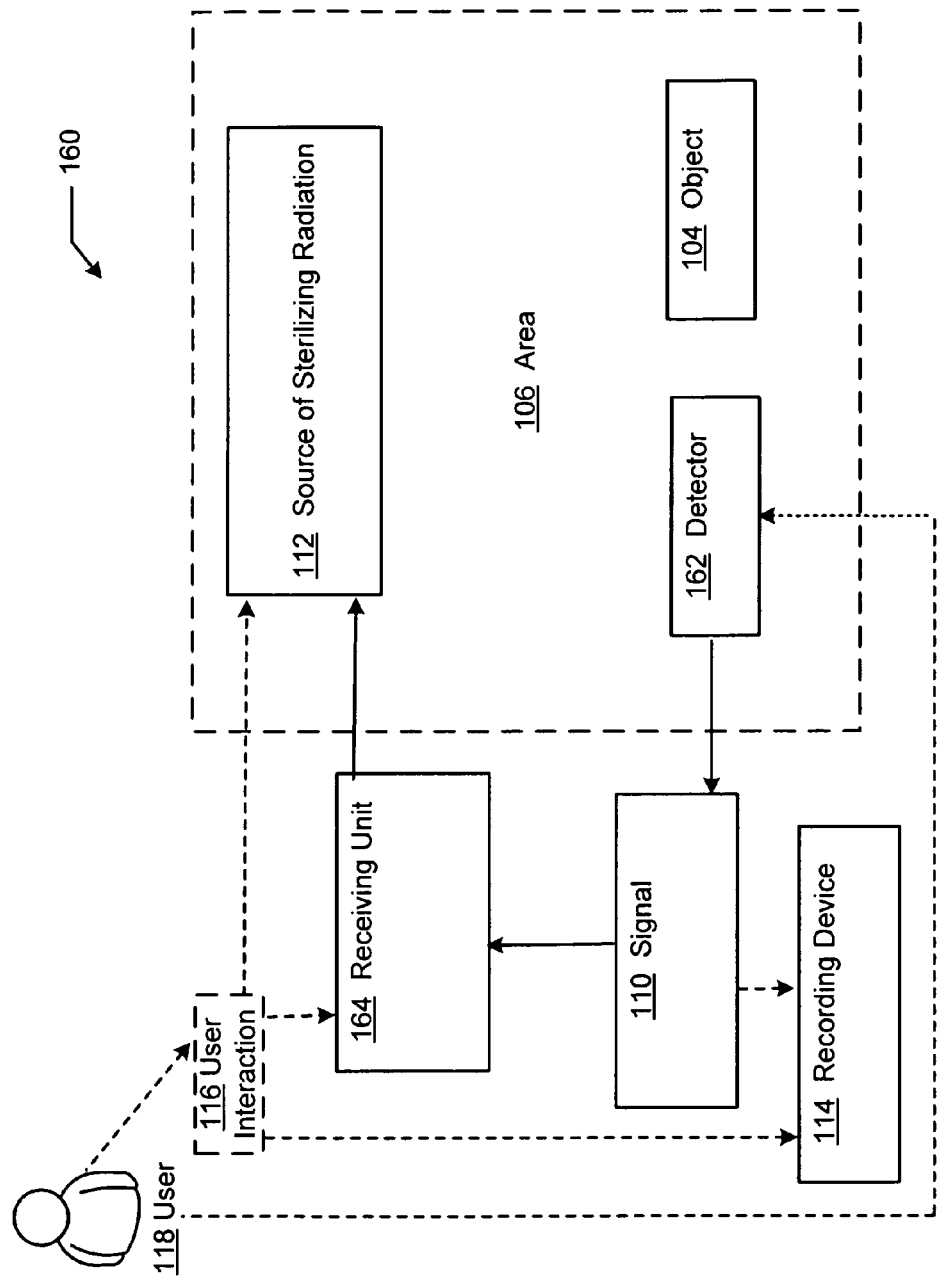
FIG. 1C illustrates an example system 160 in which embodiments may be implemented.

FIG. 1C illustrates an example system 160 in which embodiments may be implemented. In some embodiments, the system 160 is operable to provide a sterilization method that may be used to sterilize an area, a portion of an area, objects within an area, and/or substantially any combination thereof. In some embodiments, the system 160 is operable to provide a sterilization method that can be used to sterilize an area, sterilize a portion of an area, sterilize objects within an area, avoid sterilizing an area, avoid sterilizing a portion of an area, avoid sterilizing objects within an area, and/or substantially any combination thereof. In some embodiments, the system 160 is operable to sterilize an area or portion of an area 106 without exposing one or more humans present within the area or portion of the area 106 to sterilizing radiation. In some embodiments, the system 160 is operable to sterilize an area or portion of an area 106 without substantially exposing one or more humans present within the area or portion of the area 106 to sterilizing radiation.

The system 160 includes one or more detectors 162. The one or more detectors 162 can be used to detect the presence or absence of one or more objects 104 within one or more areas or portions of one or more areas 106. In some embodiments, the one or more detectors 162 can detect the presence or absence of one or more humans in one or more areas or one or more portions of one or more areas 106. In some embodiments, the one or more detectors 162 can detect if one or more shadows are present within one or more areas 106. In some embodiments, the one or more detectors 162 can detect one or more shapes that correspond to one or more objects present or absent within one or more areas 106. The one or more detectors 162 may utilize numerous technologies. For example, a detector 162 can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; computer modeling; range finders, such as laser and infrared range finders; and/or substantially any combination thereof.

The system 160 includes one or more receiving units 164. The one or more receiving units 164 can receive one or more signals 110 from one or more detectors 162. One or more sources of sterilizing radiation 112 can emit or not emit sterilizing radiation in response to one or more receiving units 164.

The other components of system 160 have been described with reference to system 100.

Figure 1D:
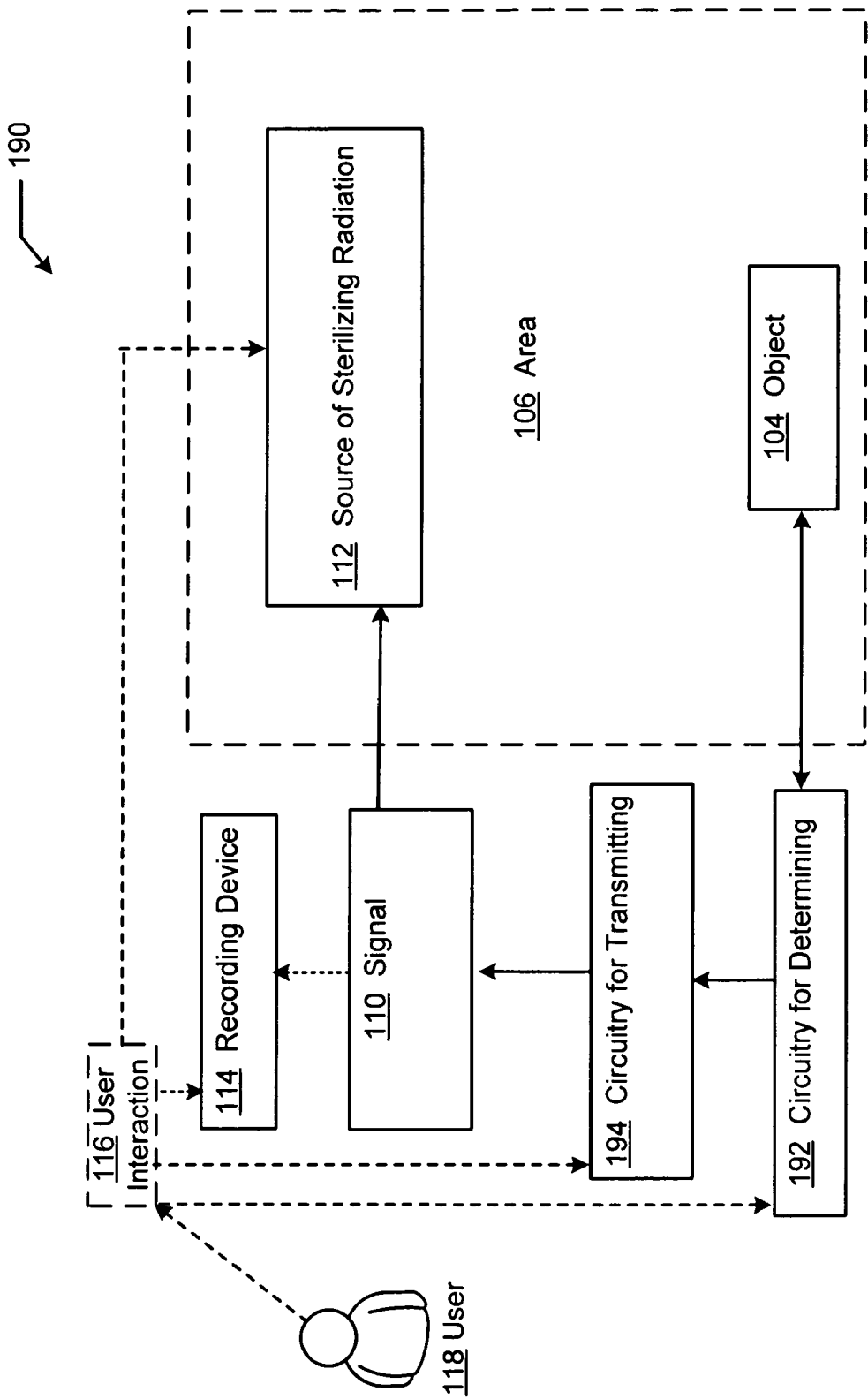
FIG. 1D illustrates an example system 190 in which embodiments may be implemented.

FIG. 1D illustrates an example system 190 in which embodiments may be implemented. In some embodiments, the system 190 is operable to provide a sterilization method that may be used to sterilize an area, a portion of an area, objects within an area, and/or substantially any combination thereof. In some embodiments, the system 190 is operable to provide a sterilization method that can be used to sterilize an area, sterilize a portion of an area, sterilize objects within an area, avoid sterilizing an area, avoid sterilizing a portion of an area, avoid sterilizing objects within an area, and/or substantially any combination thereof. In some embodiments, the system 190 is operable to sterilize an area or portion of an area 106 without exposing one or more humans present within the area or portion of the area 106 to sterilizing radiation. In some embodiments, the system 190 is operable to sterilize an area or portion of an area 106 without substantially exposing one or more humans present within the area or portion of the area 106 to sterilizing radiation.

The system 190 includes circuitry 192 for determining the presence or absence of one or more objects within one or more areas or one or more portions of one or more areas 106. In some embodiments, the circuitry 192 can determine the presence or absence of one or more humans in one or more areas or one or more portions of one or more areas 106. In some embodiments, the circuitry 192 can determine if one or more shadows are present within one or more areas 106. In some embodiments, the circuitry 192 can determine one or more shapes that correspond to one or more objects present or absent within one or more areas 106. The circuitry 192 may utilize numerous technologies. For example, the circuitry 192 can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; computer modeling; range finders, such as laser and infrared range finders; and/or substantially any combination thereof.

The system 190 includes circuitry for transmitting one or more signals 110 to one or more sources of sterilizing radiation 112. One or more sources of sterilizing radiation 112 can emit or not emit sterilizing radiation in response to the signal from the circuitry for transmitting 194. The circuitry for transmitting 194 can transmit numerous types of signals 110 to one or more sources of sterilizing radiation 112. For example, the circuitry for transmitting 194 can transmit a signal 110 that includes, but is not limited to, a hardwired signal, an infrared signal, an optical signal, a radiofrequency (RF) signal, a digital signal, an analog signal, or substantially any combination thereof to one or more sources of sterilizing radiation 112.

The system 190 may include one or more recording devices 114. In some embodiments, the one or more recording devices 114 communicate with the circuitry for transmitting 194, communicate with the circuitry for determining 192 or communicate with both the circuitry for transmitting 194 and the circuitry for determining 192.

The other components of system 190 have been described with reference to system 100.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 2:
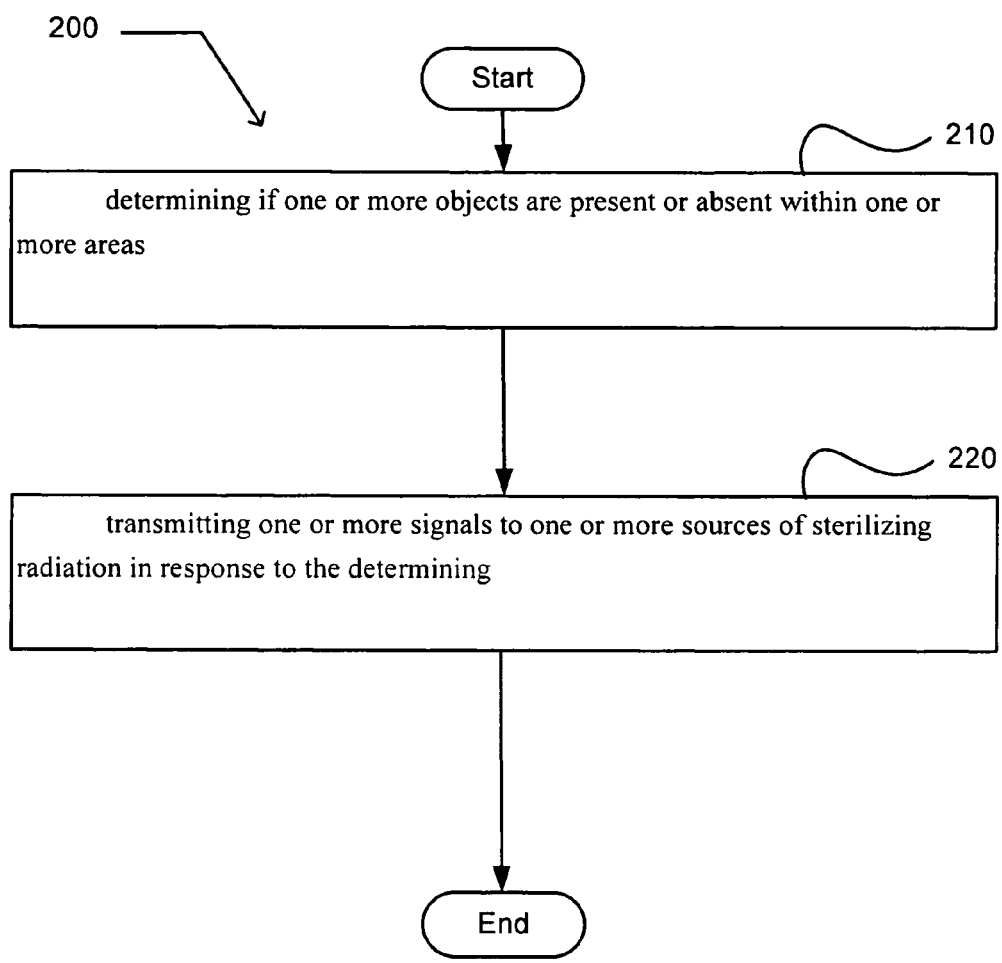
FIG. 2 illustrates an operational flow representing example operations related to sterilization methods.

FIG. 2 illustrates an operational flow 200 representing examples of operations that are related to the performance of a sterilization method. In FIG. 2 and in following figures that include various examples of operations used during performance of the sterilization method, discussion and explanation may be provided with respect to the above-described example of FIG. 1A, and/or with respect to other examples and contexts. However, it should be understood that the operations may be executed in a number of other environments and contexts, and/or modified versions of FIG. 1A. Also, although the various operations are presented in the sequence(s) illustrated, it should be understood that the various operations may be performed in other orders than those which are illustrated, or may be performed concurrently.

After a start operation, the operational flow 200 includes an operation 210 involving determining if one or more objects are present or absent within one or more areas. In some embodiments, one or more determining units act to determine if one or more objects are present or absent in one or more areas. In some embodiments, a single determining unit acts to determine the presence or absence of one or more objects within one area. In some embodiments, a single determining unit acts to determine the presence or absence of one or more objects within two or more areas. In some embodiments, two or more determining units act to determine the presence or absence of one or more objects within one area. In some embodiments, two or more determining units act to determine the presence or absence of one or more objects within two or more areas.

The operational flow 200 also includes a transmitting operation 220 involving transmitting one or more signals to one or more sources of sterilizing radiation in response to the determining. In some embodiments, one or more transmitting units transmit one or more signals to one or more sources of sterilizing radiation in response to the determining operation. Accordingly, in some embodiments, one transmitting unit can transmit one or more signals to a single source of sterilizing radiation or to numerous sources of sterilizing radiation. For example, in some embodiments, one transmitting unit transmits one signal to one source of sterilizing radiation. In some embodiments, one transmitting unit transmits more than one signal to one source of sterilizing radiation. In other embodiments, one transmitting unit transmits one signal to more than one source of sterilizing radiation. In still other embodiments, one transmitting unit transmits more than one signal to more than one source of sterilizing radiation. In addition, two or more transmitting units can each transmit one or more signals to a single source of sterilizing radiation or to numerous sources of sterilizing radiation. For example, in some embodiments, two or more transmitting units can each transmit one or more signals to a single source of sterilizing radiation. In some embodiments, two or more transmitting units can each transmit one or more signals to numerous sources of sterilizing radiation.

Figure 3:
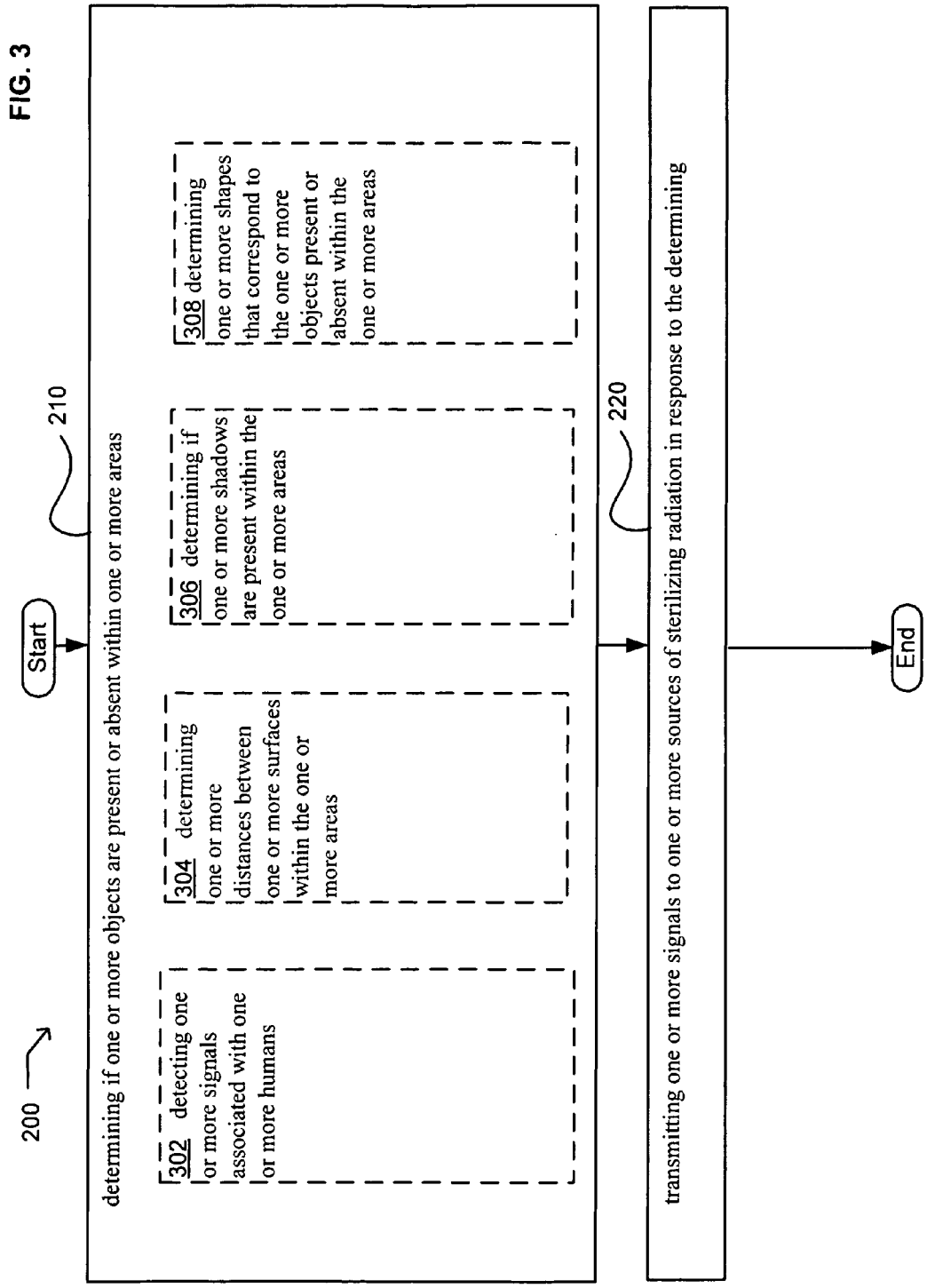
FIG. 3 illustrates an alternative embodiment of the example operation flow of FIG. 2.

FIG. 3 illustrates alternative embodiments of the example operational flow 200 of FIG. 2. FIG. 3 illustrates example embodiments where the determining operation 210 may include at least one additional operation. Additional operations may include an operation 302, an operation 304, an operation 306, and/or an operation 308.

At operation 302, the determining operation 210 may include detecting one or more signals associated with one or more humans. In some embodiments, one or more determining units are used to detect one or more signals associated with one or more humans. In some embodiments, one signal associated with a human can be detected. In some embodiments, one or more signals associated with a human can be detected. In some embodiments, one or more signals associated with one or more humans can be detected. In other embodiments, detecting at least one signal associated with a human includes detecting the absence of any signal associated with a human. For example, the absence of one or more humans from an area can be detected.

Numerous signals that are associated with one or more humans can be detected. Examples of such signals include, but are not limited to, infrared radiation, retinal reflection, motion detection, profile detection, and substantially any combination thereof. In some embodiments, a tag that is attached to a human can be detected to indicate the presence or absence of a human in one or more areas. For example, a tag can transmit a signal that is recognized by a determining unit to provide for determining if one or more humans are present or absent in one or more areas. In other embodiments, the presence or absence of a human in one or more areas can be detected through use of an access device that is used to enter one or more areas. For example, an access card, key pad, lock, or other device coupled to entry of a human into an area can be detected by the determining unit to indicate the presence or absence of a human within the area.

At operation 304, the determining operation 210 may include determining one or more distances between one or more surfaces within the one or more areas. In some embodiments, one or more determining units are used to determine one or more distances between one or more surfaces within the one or more areas. Such determining can include approximation of such distances. Numerous methods can be used to determine distances between surfaces within an area. In some embodiments, computer modeling can be used to determine the dimensions of an area and distances between surfaces within the area. In other embodiments, the distances between surfaces contained within an area can be determined through use of other methods, and combinations of methods, that include laser range finding, sonar, radar, and the like. The determination of distances to surfaces within an area allows the position of objects within the area to be modeled. In addition, determination of distances to surfaces within an area allows sterilizing radiation to be adjusted in accordance with a determined distance.

At operation 306, the determining operation 210 may include determining if one or more shadows are present within the one or more areas. In some embodiments, one or more determining units are used to determine if one or more shadows are present within the one or more areas. Shadows may occur when incident radiation is blocked from irradiating a portion of an area by an object positioned between the source of radiation and the portion of the area. Determining the existence of such shadows allows portions of an area that will not be sterilized by incident radiation to be predicted and assigned non-sterile status. Alternatively, determining the existence of such shadows provides for the irradiation of the shadows with sterilizing radiation emitted from a second source of sterilizing radiation. Such determining can include computer modeling to determine if radiation, such as ultraviolet light, emitted from a source of sterilizing radiation at an assigned position will impinge on a given portion of the area. Additional methods may be used to determine if one or more shadows are present within an area that include the use of sensors positioned throughout the area, use of indicators that phosphoresce or change color when irradiated, and the like.

At operation 308, the determining operation 210 may include determining one or more shapes that correspond to the one or more objects present or absent in the one or more areas. In some embodiments, one or more determining units are used to determine one or more shapes that correspond to the one or more objects present or absent in the one or more areas. Objects present within an area can be of various shapes that may affect their ability to be sterilized by being irradiated with sterilizing radiation. Accordingly, determination of the shape of an object provides for the adjustment of sterilizing radiation so that it is incident on the object in order that the object can be more adequately sterilized. For example, a beam of sterilizing radiation may be adjusted so that it is directed on channels that are included within an object such that the spaces within the channels are adequately sterilized with the sterilizing radiation. The shape of an object may be determined through use of numerous techniques. For example, in some embodiments, computer modeling can be used to determine the shape of objects that are present in an area. In other embodiments, shapes that correspond to the one or more objects present in an area can be determined through use of photographic methods, optical methods, and the like. Numerous objects may be present or absent within one or more areas or one or more portions of one or more areas. Examples of such objects include, but are not limited to, humans, non-human animals, plants, surgical instruments, cooking utensils, eating utensils, sinks, tables, machinery, waste areas, and the like.

Figure 4:
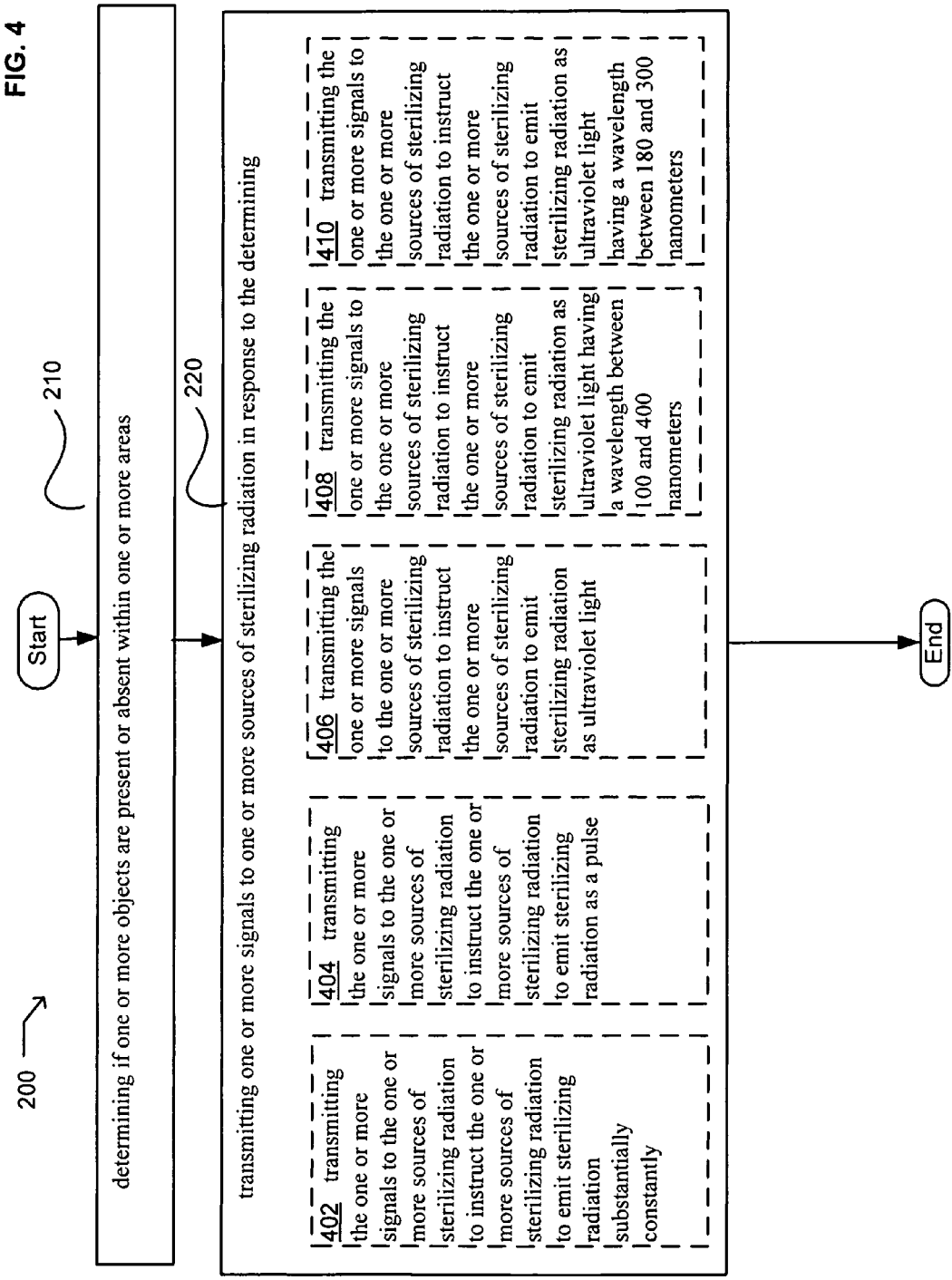
FIG. 4 illustrates an alternative embodiment of the example operation flow of FIG. 2.

FIG. 4 illustrates alternative embodiments of the example operational flow 200 of FIG. 2. FIG. 4 illustrates example embodiments where the transmitting operation 220 may include at least one additional operation. Additional operations may include an operation 402, an operation 404, an operation 406, an operation 408, and/or an operation 410.

At operation 402, the transmitting operation 220 may include transmitting one or more signals to one or more sources of sterilizing radiation to instruct the one or more sources of sterilizing radiation to emit sterilizing radiation substantially constantly. In some embodiments, one or more transmitting units are used to transmit one or more signals to one or more sources of sterilizing radiation. In such instances, one or more sources of sterilizing radiation will emit radiation in a manner that does not involve the alternating emission and non-emission of radiation according to a substantially cyclic pattern. However, such emission may be started and stopped, intensity modulated, paused, initiated, interrupted, resumed, programmed to follow a preprogrammed schedule, routine or sequence, or substantially any combination thereof. In contrast to constant emission, radiation emitted in a pulsed manner involves emission and non-emission of radiation according to a substantially cyclic repeated pattern.

At operation 404, the transmitting operation 220 may include transmitting one or more signals to one or more sources of sterilizing radiation to instruct the one or more sources of sterilizing radiation to emit sterilizing radiation as a pulse. In some embodiments, one or more transmitting units are used to transmit one or more signals to one or more sources of sterilizing radiation. In such instances, radiation will be emitted from the one or more sources of sterilizing radiation according to a substantially cyclic program that includes an alternating period of emission followed by a period of non-emission. For example, radiation is emitted in flashes that occur at specifically spaced time points. Emission of radiation that is emitted as a pulse may be started and stopped, intensity modulated, paused, initiated, interrupted, resumed, programmed to follow a preprogrammed schedule, routine or sequence, and substantially any combination thereof. In some embodiments, emission of radiation in a pulsed manner may be used to reduce heat output associated with a source of sterilizing radiation.

At operation 406, the transmitting operation 220 may include transmitting one or more signals to one or more sources of sterilizing radiation to instruct the one or more sources of sterilizing radiation to emit sterilizing radiation as ultraviolet light. In some embodiments, one or more transmitting units are used to transmit one or more signals to one or more sources of sterilizing radiation. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 408, the transmitting operation 220 may include transmitting one or more signals to one or more sources of sterilizing radiation to instruct the one or more sources of sterilizing radiation to emit sterilizing radiation as ultraviolet light having a wavelength between 100 and 400 nanometers. In some embodiments, one or more transmitting units are used to transmit one or more signals to one or more sources of sterilizing radiation to instruct the one or more sources of sterilizing radiation to emit sterilizing radiation as ultraviolet light. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 410, the transmitting operation 220 may include transmitting one or more signals to one or more sources of sterilizing radiation to instruct the one or more sources of sterilizing radiation to emit sterilizing radiation as ultraviolet light having a wavelength between 180 and 300 nanometers. In some embodiments, one or more transmitting units are used to transmit one or more signals to one or more sources of sterilizing radiation to instruct the one or more sources of sterilizing radiation to emit sterilizing radiation as ultraviolet light having a wavelength between 180 and 300 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

Figure 5:
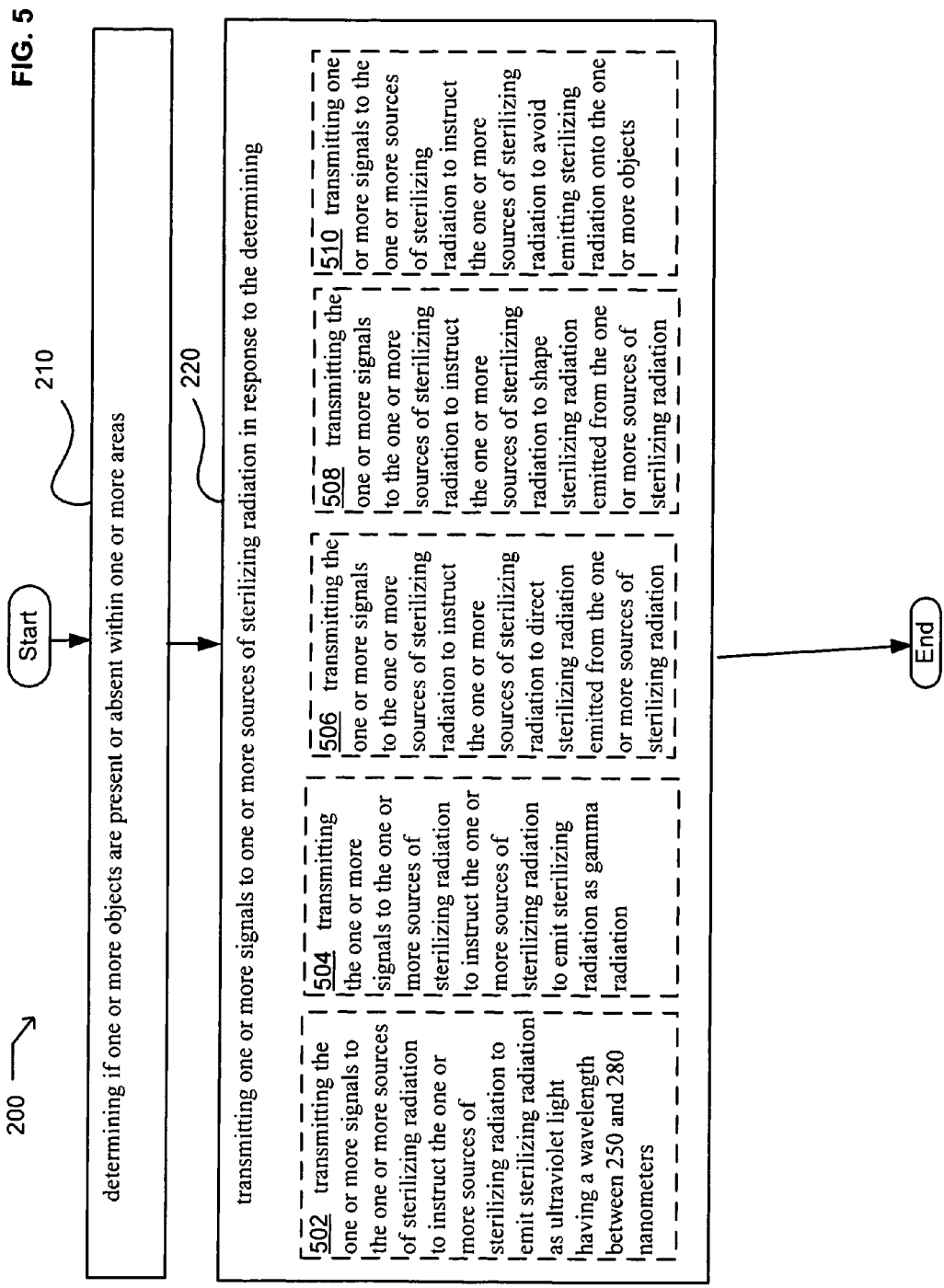
FIG. 5 illustrates an alternative embodiment of the example operation flow of FIG. 2.

FIG. 5 illustrates alternative embodiments of the example operational flow 200 of FIG. 2. FIG. 5 illustrates example embodiments where the transmitting operation 220 may include at least one additional operation. Additional operations may include an operation 502, an operation 504, an operation 506, an operation 508, and/or an operation 510.

At operation 502, the transmitting operation 220 may include transmitting one or more signals to one or more sources of sterilizing radiation to instruct the one or more sources of sterilizing radiation to emit sterilizing radiation as ultraviolet light having a wavelength between 250 and 280 nanometers. In some embodiments, one or more transmitting units are used to transmit one or more signals to one or more sources of sterilizing radiation to instruct the one or more sources of sterilizing radiation to emit sterilizing radiation as ultraviolet light having a wavelength between 250 and 280 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 504, the transmitting operation 220 may include transmitting one or more signals to one or more sources of sterilizing radiation to instruct the one or more sources of sterilizing radiation to emit sterilizing radiation as gamma radiation. In some embodiments, one or more transmitting units are used to transmit one or more signals to one or more sources of sterilizing radiation. Gamma radiation may be emitted from a source of sterilizing radiation that includes Cobalt-60. Such sources are known and are commercially available (MDS Nordion, Ottawa, Ontario, Canada).

At operation 506, the transmitting operation 220 may include transmitting the one or more signals to the one or more sources of sterilizing radiation to instruct the one or more sources of sterilizing radiation to direct sterilizing radiation emitted from the one or more sources of sterilizing radiation. In some embodiments, one or more transmitting units are used to transmit one or more signals to one or more sources of sterilizing radiation to direct sterilizing radiation emitted from the one or more sources of sterilizing radiation. In some embodiments, the sterilizing radiation is directed such that it impinges on a portion of an area. In some embodiments, the sterilizing radiation is directed away from one or more objects or surfaces. In some embodiments, the sterilizing radiation is focused such that it impinges on one or more defined surfaces or objects. Focusing of sterilizing radiation can serve to increase the intensity of sterilizing radiation impinging on a given area. Accordingly, sterilizing radiation may be intensified on an area or portion of an area in need of such treatment.

At operation 508, the transmitting operation 220 may include transmitting one or more signals to one or more sources of sterilizing radiation to instruct the one or more sources of sterilizing radiation to shape sterilizing radiation emitted from the one or more sources of sterilizing radiation. In some embodiments, one or more transmitting units are used to transmit one or more signals to one or more sources of sterilizing radiation to shape sterilizing radiation emitted from the one or more sources of sterilizing radiation. Sterilizing radiation may be shaped though use of numerous methods. For example, lenses and mirrors can be used to shape sterilizing radiation. Accordingly, the spatial distribution of sterilizing radiation can be controlled. In some embodiments, the sterilizing radiation is shaped such that one or more specific areas or objects are irradiated. In some embodiments, the sterilizing radiation is shaped to avoid irradiating one or more specific areas or objects. In some embodiments, the sterilization radiation is shaped into a beam that can be swept to sterilize one or more areas or one or more portions of one or more areas.

At operation 510, the transmitting operation 220 may include transmitting one or more signals to the one or more sources of sterilizing radiation to instruct the one or more sources of sterilizing radiation to avoid emitting sterilizing radiation onto the one or more objects. In some embodiments, one or more transmitting units are used to transmit one or more signals to one or more sources of sterilizing radiation to avoid emitting sterilizing radiation onto the one or more objects. Numerous objects may be present or absent within one or more areas or one or more portions of one or more areas. Examples of such objects include, but are not limited to, humans, non-human animals, plants, surgical instruments, cooking utensils, eating utensils, sinks, tables, machinery, waste areas, and the like.

Figure 6:
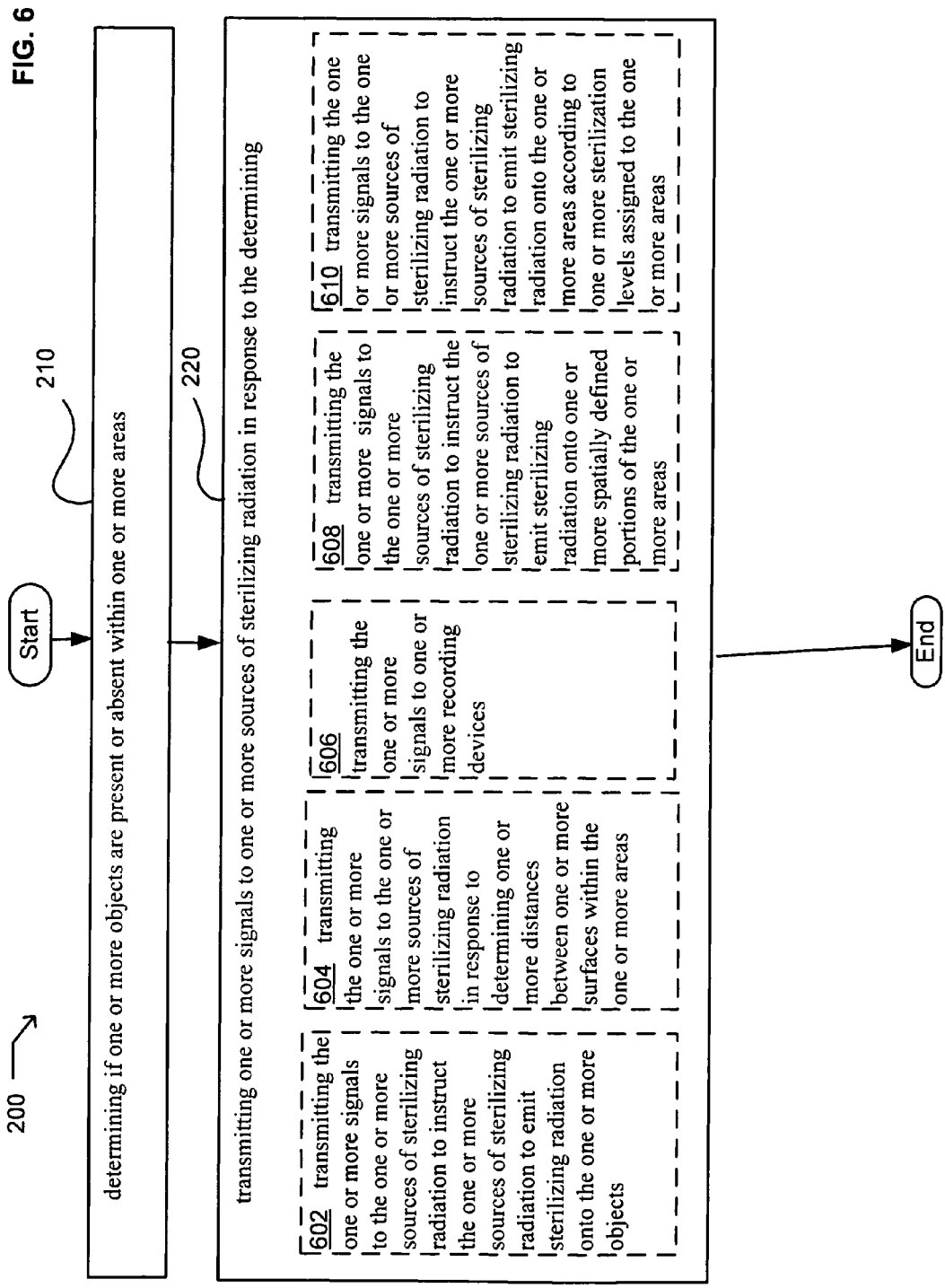
FIG. 6 illustrates an alternative embodiment of the example operation flow of FIG. 2.

FIG. 6 illustrates alternative embodiments of the example operational flow 200 of FIG. 2. FIG. 6 illustrates example embodiments where the transmitting operation 220 may include at least one additional operation. Additional operations may include an operation 602, an operation 604, an operation 606, an operation 608, and/or an operation 610.

At operation 602, the transmitting operation 220 may include transmitting one or more signals to one or more sources of sterilizing radiation to instruct the one or more sources of sterilizing radiation to emit sterilizing radiation onto the one or more objects. In some embodiments, one or more transmitting units are used to transmit one or more signals to one or more sources of sterilizing radiation instructing the one or more sources of sterilizing radiation to emit sterilizing radiation onto the one or more surfaces. Numerous objects may be present or absent within one or more areas or one or more portions of one or more areas. Examples of such objects include, but are not limited to, humans, non-human animals, plants, surgical instruments, cooking utensils, eating utensils, sinks, tables, machinery, waste areas, and the like.

At operation 604, the transmitting operation 220 may include transmitting one or more signals to one or more sources of sterilizing radiation in response to determining one or more distances between one or more surfaces within the one or more areas. In some embodiments, one or more transmitting units are used to transmit one or more signals to one or more sources of sterilizing radiation in response to determining one or more distances between one or more surfaces within the one or more areas. The one or more transmitting units respond to one or more determining units that determine one or more distances between one or more surfaces within the one or more areas.

At operation 606, the transmitting operation 220 may include transmitting the one or more signals to one or more recording devices. In some embodiments, one or more transmitting units are used to transmit one or more signals to one or more recording devices. Many types of recording devices may be used. Examples of such recording devices include, but are not limited to, many types of memory, optical disks, magnetic disks, magnetic tape, and the like. In some embodiments, one or more recording devices provide for user interaction. In some embodiments, the signal includes information associated with frequency of sterilization, intensity of sterilization, area of sterilization, and the like.

At operation 608, the transmitting operation 220 may include transmitting the one or more signals to the one or more sources of sterilizing radiation to instruct the one or more sources of sterilizing radiation to emit sterilizing radiation onto one or more spatially defined portions of the one or more areas. In some embodiments, one or more transmitting units are used to transmit one or more signals to one or more sources of sterilizing radiation to instruct the one or more sources of sterilizing radiation to emit sterilizing radiation onto one or more spatially defined portions of the one or more areas. Examples of such areas include, but are not limited to, hospitals, such as operating rooms and wards; transportation, such as airplanes, trains, cars, subways, buses; kitchens; bathrooms; and the like. Examples of spatially defined portions of one or more areas include, but are not limited to, one or more sinks within one or more operating rooms, one or more tables within one or more operating rooms, one or more portions of flooring within one or more operating rooms, one or more portions of siding within one or more operating rooms, and the like.

At operation 610, the transmitting operation 220 may include transmitting the one or more signals to the one or more sources of sterilizing radiation to instruct the one or more sources of sterilizing radiation to emit sterilizing radiation onto the one or more areas according to one or more sterilization levels assigned to the one or more areas. In some embodiments, one or more transmitting units are used to transmit one or more signals to one or more sources of sterilizing radiation to instruct the one or more sources of sterilizing radiation to emit sterilizing radiation onto the one or more areas according to one or more sterilization levels assigned to the one or more areas. One or more sterilization levels may be assigned to one or more areas according to the degree of sterility desired for the one or more areas. For example, an operating room in a hospital may receive a high sterilization level while a reception room may receive a low sterilization level.

Figure 7:
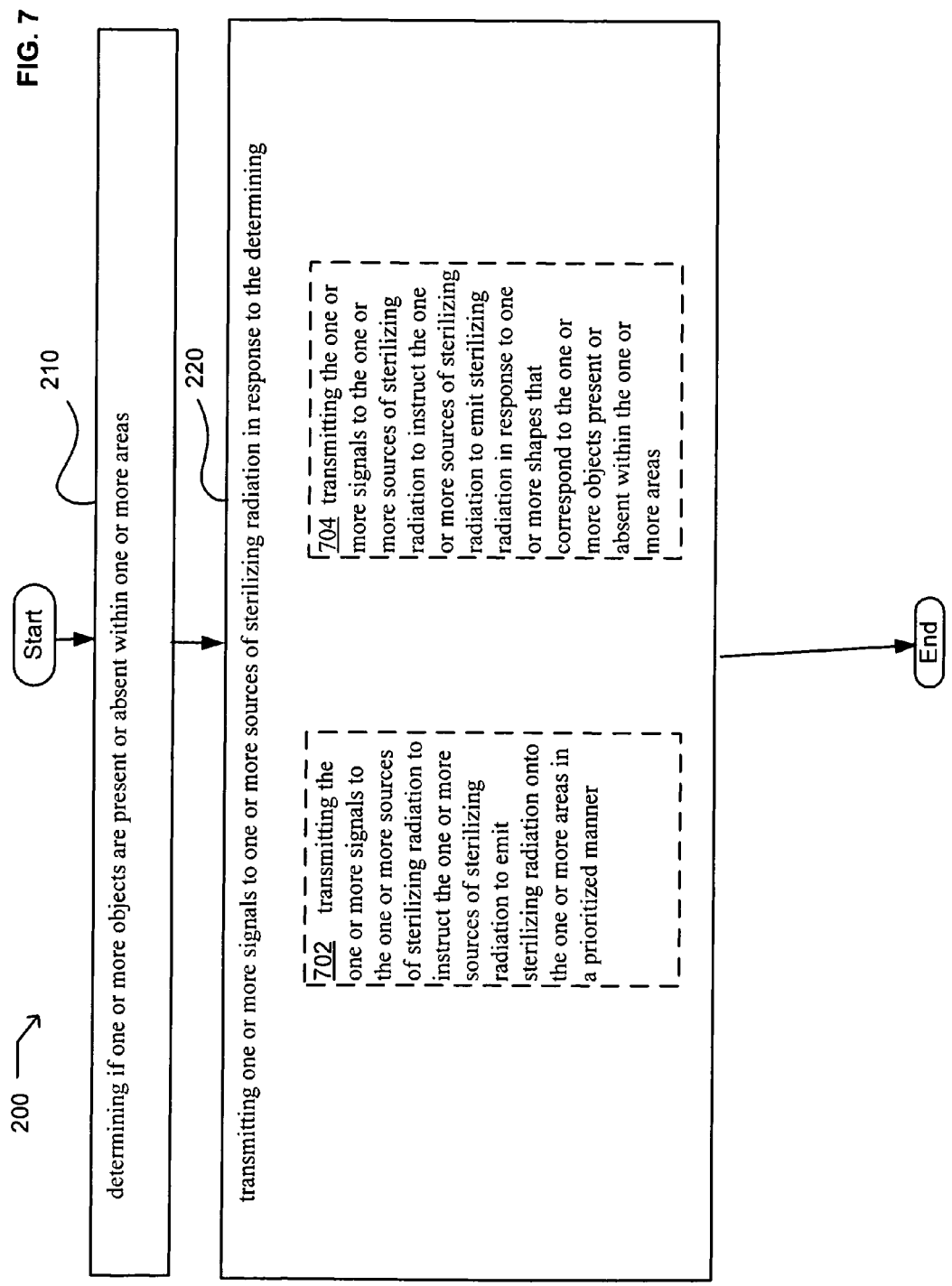
FIG. 7 illustrates an alternative embodiment of the example operation flow of FIG. 2.

FIG. 7 illustrates alternative embodiments of the example operational flow 200 of FIG. 2. FIG. 7 illustrates example embodiments where the transmitting operation 220 may include at least one additional operation. Additional operations may include an operation 702, and/or an operation 704.

At operation 702, the transmitting operation 220 may include transmitting the one or more signals to the one or more sources of sterilizing radiation to instruct the one or more sources of sterilizing radiation to emit sterilizing radiation onto the one or more areas in a prioritized manner. In some embodiments, one or more transmitting units are used to transmit one or more signals to one or more sources of sterilizing radiation to instruct the one or more sources of sterilizing radiation to emit sterilizing radiation onto the one or more areas in a prioritized manner. In some embodiments, a prioritized manner includes irradiating one or more areas with respect to immediacy, latency, intensity, and the like. In some embodiments, a prioritized manner includes irradiating one or more areas with regard to time-integrated intensity of sterilizing radiation such as irradiation of one or more areas as functions of either relative or absolute locations in the reference enclosed volume so that high-patient-hazard or high-infectivity-likelihood areas and volumes can be specified for the most rigorous and/or frequent irradiation.

At operation 704, the transmitting operation 220 may include transmitting the one or more signals to the one or more sources of sterilizing radiation to instruct the one or more sources of sterilizing radiation to emit sterilizing radiation in response to one or more shapes that correspond to the one or more objects present or absent within the one or more areas. In some embodiments, one or more determining units are used to determine one or more shapes that correspond to the one or more objects present or absent within the one or more areas. In some embodiments, one or more transmitting units are used to transmit one or more signals to one or more sources of sterilizing radiation to instruct the one or more sources of sterilizing radiation to emit sterilizing radiation in response to one or more shapes that correspond to the one or more objects present or absent within the one or more areas. Objects present within an area can be of various shapes that may affect their ability to be sterilized by being irradiated with sterilizing radiation. Accordingly, determination of the shape of an object provides for the adjustment of sterilizing radiation so that it is incident on the object in order that the object can be more adequately sterilized. For example, a beam of sterilizing radiation may be adjusted so that it is directed on channels that are included within an object such that the spaces within the channels are adequately sterilized with the sterilizing radiation. The shape of an object may be determined through use of numerous techniques. For example, in some embodiments, computer modeling can be used to determine the shape of objects that are present in an area. In other embodiments, shapes that correspond to the one or more objects present in an area can be determined through use of photographic methods, optical methods, and the like.

Figure 8:
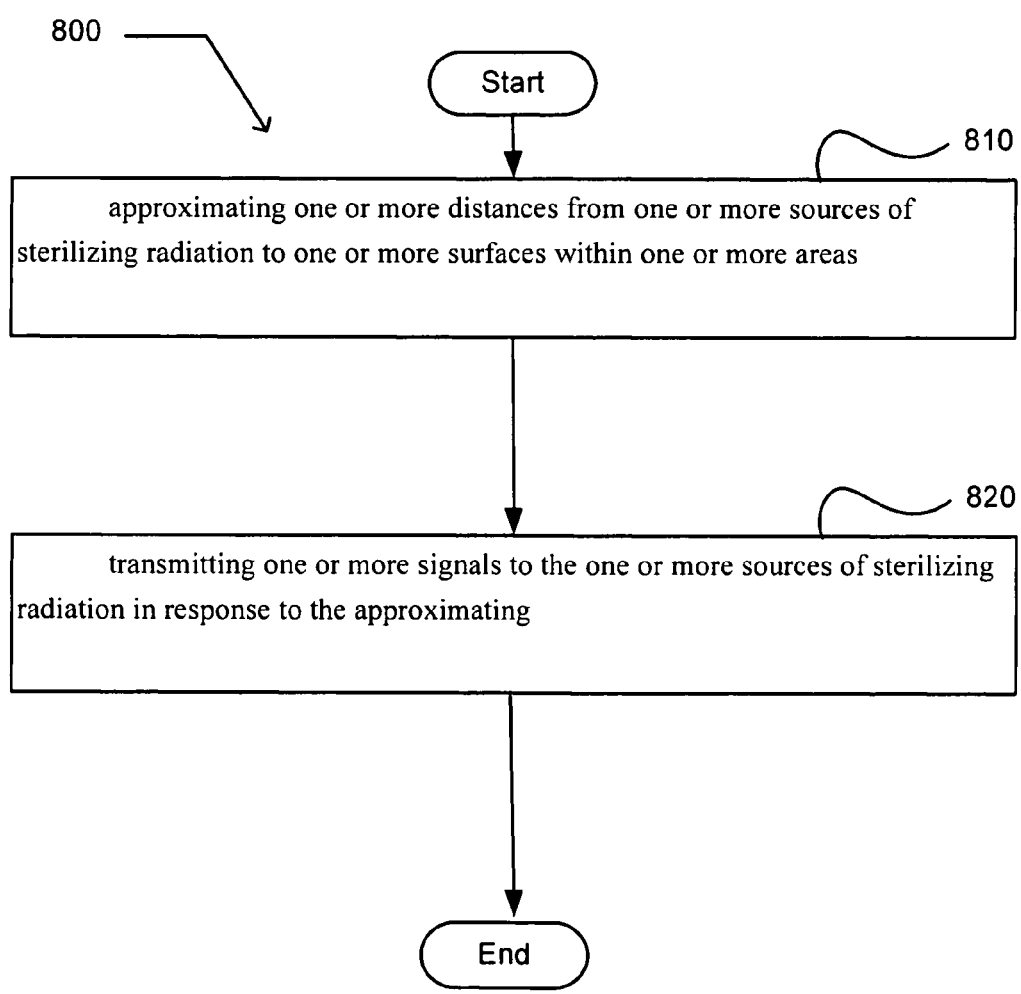
FIG. 8 illustrates an operational flow representing example operations related to sterilization methods.

FIG. 8 illustrates an operational flow 800 representing examples of operations that are related to the performance of a sterilization method. In FIG. 8 and in following figures that include various examples of operations used during performance of the sterilization method, discussion and explanation may be provided with respect to the above-described example of FIG. 1B, and/or with respect to other examples and contexts. However, it should be understood that the operations may be executed in a number of other environments and contexts, and/or modified versions of FIG. 1B. Also, although the various operations are presented in the sequence(s) illustrated, it should be understood that the various operations may be performed in other orders than those which are illustrated, or may be performed concurrently.

After a start operation, the operational flow 800 includes an approximating operation 810 involving approximating one or more distances from one or more sources of sterilizing radiation to one or more surfaces within one or more areas. In some embodiments, one or more approximating units act to approximate one or more distances from one or more sources of sterilizing radiation to one or more surfaces within one or more areas. In some embodiments, a single approximating unit acts to approximate one or more distances from one or more sources of sterilizing radiation to one or more surfaces within one or more areas. In some embodiments, two or more approximating units act to approximate one or more distances from one or more sources of sterilizing radiation to one or more surfaces within one or more areas. In some embodiments, two or more approximating units act to approximate one or more distances from one or more sources of sterilizing radiation to one or more surfaces within one or more areas.

The operational flow 800 also includes a transmitting operation 820 involving transmitting one or more signals to the one or more sources of sterilizing radiation in response to the approximating. In some embodiments, one or more transmitting units transmit one or more signals to one or more sources of sterilizing radiation in response to the approximating operation 810. Accordingly, in some embodiments, one transmitting unit can transmit one or more signals to a single source of sterilizing radiation or to numerous sources of sterilizing radiation. For example, in some embodiments, one transmitting unit transmits one signal to one source of sterilizing radiation. In some embodiments, one transmitting unit transmits more than one signal to one source of sterilizing radiation. In other embodiments, one transmitting unit transmits one signal to more than one source of sterilizing radiation. In still other embodiments, one transmitting unit transmits more than one signal to more than one source of sterilizing radiation. In addition, two or more transmitting units can each transmit one or more signals to a single source of sterilizing radiation or to numerous sources of sterilizing radiation. For example, in some embodiments, two or more transmitting units can each transmit one or more signals to a single source of sterilizing radiation. In some embodiments, two or more transmitting units can each transmit one or more signals to numerous sources of sterilizing radiation.

Figure 9:
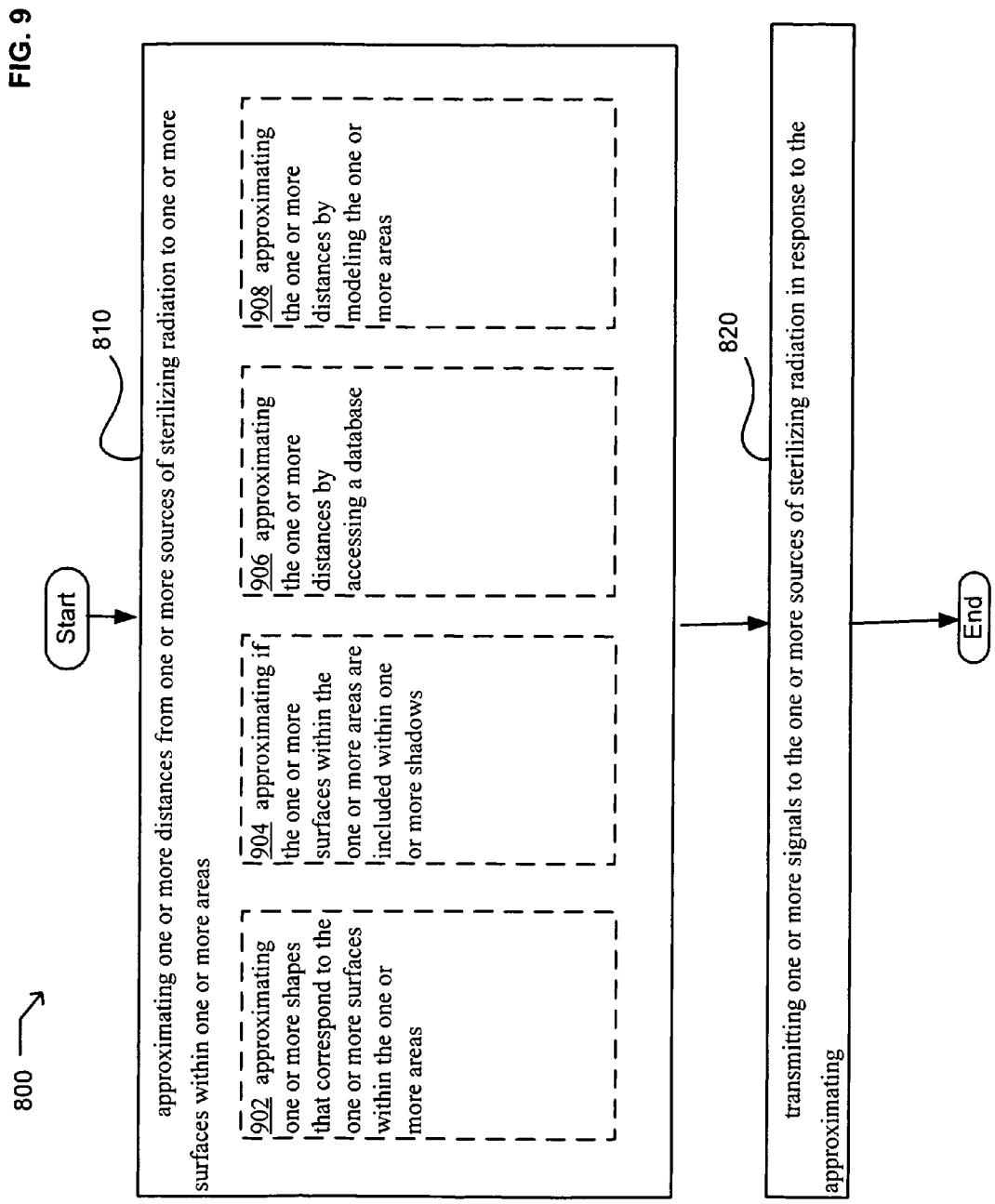
FIG. 9 illustrates an alternative embodiment of the example operation flow of FIG. 8.

FIG. 9 illustrates alternative embodiments of the example operational flow 800 of FIG. 8. FIG. 9 illustrates example embodiments where the approximating operation 810 may include at least one additional operation. Additional operations may include an operation 902, an operation 904, an operation 906, and/or an operation 908.

At operation 902, the approximating operation 810 may include approximating one or more shapes that correspond to the one or more surfaces within the one or more areas. In some embodiments, one or more approximating units can approximate distances between one or more shapes that correspond to one or more surfaces of one or more objects present or absent within one or more areas. The one or more approximating units may utilize numerous technologies. For example, an approximating unit can use technologies that include, but are not limited to, infrared radiation, such as long-wave infrared radiation; retinal reflection; corneal reflection; tag readers, such as card readers, badge readers, bar code readers, and the like; motion detection; radar detection; sonar detection; computer modeling; range finders, such as laser and infrared range finders; and/or substantially any combination thereof. The approximated distances can be used to direct sterilizing radiation onto or away from one or more objects or surfaces.

At operation 904, the approximating operation 810 may include approximating if the one or more surfaces within the one or more areas are included within one or more shadows. In some embodiments, one or more approximating units are used to determine if one or more surfaces within one or more areas are included within one or more shadows present within the one or more areas. Shadows may occur when incident radiation is blocked from irradiating a portion of an area by an object positioned between the source of radiation and the portion of the area. Determining the existence of such shadows allows portions of an area that will not be sterilized by incident radiation to be predicted and assigned non-sterile status. Alternatively, determining the existence of such shadows provides for the irradiation of the shadows with sterilizing radiation emitted from a second source of sterilizing radiation. Such determining can include computer modeling to determine if radiation, such as ultraviolet light, emitted from a source of sterilizing radiation at an assigned position will impinge on a given portion of the area. Additional methods may be used to determine if one or more shadows are present within an area that include the use of sensors positioned throughout the one or more areas, use of indicators that phosphoresce or change color when irradiated, and the like.

At operation 906, the approximating operation 810 may include approximating the one or more distances by accessing a database. In some embodiments, one or more approximating units are used to approximate one or more distances by accessing a database. In some embodiments, a database will include coordinates for one or more surfaces and/or one or more objects within one or more areas. In some embodiments, a database will include measured distances for one or more surfaces and/or one or more objects within one or more areas.

At operation 908, the approximating operation 810 may include approximating the one or more distances by modeling the one or more areas. In some embodiments, one or more approximating units are used to approximate the one or more distances by modeling the one or more areas. In some embodiments, computer modeling may be used to model one or more surfaces within one or more areas, one or more objects within one or more areas, one or more areas, one or more portions of one or more areas and substantially any combination thereof.

Figure 10:
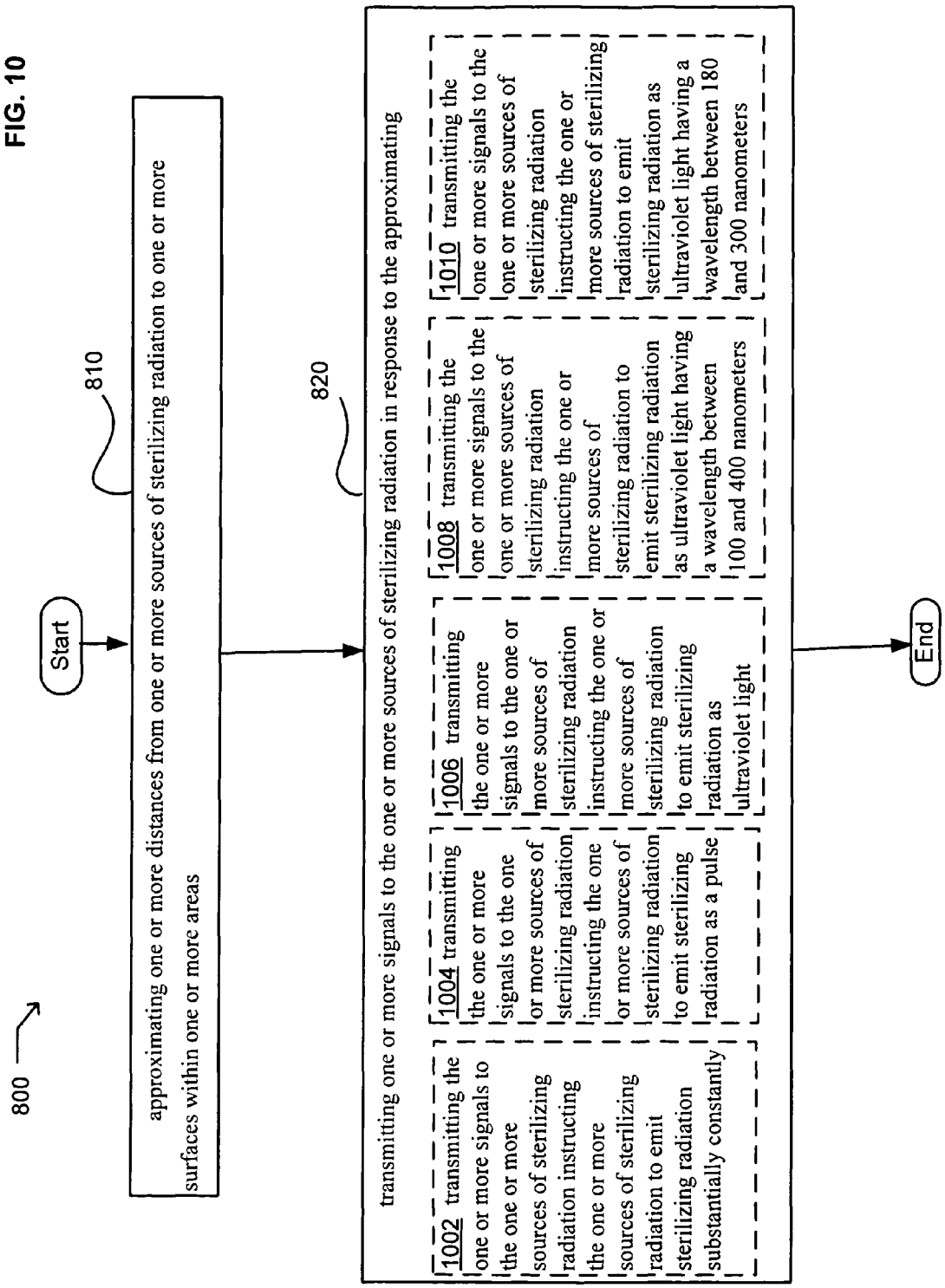
FIG. 10 illustrates an alternative embodiment of the example operation flow of FIG. 8.

FIG. 10 illustrates alternative embodiments of the example operational flow 800 of FIG. 8. FIG. 10 illustrates example embodiments where the transmitting operation 820 may include at least one additional operation. Additional operations may include an operation 1002, an operation 1004, an operation 1006, an operation 1008, and/or an operation 1010.

At operation 1002, the transmitting operation 820 may include transmitting the one or more signals to the one or more sources of sterilizing radiation instructing the one or more sources of sterilizing radiation to emit sterilizing radiation substantially constantly. In some embodiments, one or more transmitting units are used to transmit the one or more signals to the one or more sources of sterilizing radiation. In such instances, one or more sources of sterilizing radiation will emit radiation in a manner that does not involve the alternating emission and non-emission of radiation according to a substantially cyclic pattern. However, such emission may be started and stopped, intensity modulated, paused, initiated, interrupted, resumed, programmed to follow a preprogrammed schedule, routine or sequence, or substantially any combination thereof. In contrast to constant emission, radiation emitted in a pulsed manner involves emission and non-emission of radiation according to a substantially cyclic repeated pattern.

At operation 1004, the transmitting operation 820 may include transmitting the one or more signals to the one or more sources of sterilizing radiation instructing the one or more sources of sterilizing radiation to emit sterilizing radiation as a pulse. In some embodiments, one or more transmitting units are used to transmit the one or more signals to the one or more sources of sterilizing radiation. In such instances, radiation will be emitted from the one or more sources of sterilizing radiation according to a substantially cyclic program that includes an alternating period of emission followed by a period of non-emission. For example, radiation is emitted in flashes that occur at specifically spaced time points. Emission of radiation that is emitted as a pulse may be started and stopped, intensity modulated, paused, initiated, interrupted, resumed, programmed to follow a preprogrammed schedule, routine or sequence, and substantially any combination thereof. In some embodiments, emission of radiation in a pulsed manner may be used to reduce heat output associated with a source of sterilizing radiation.

At operation 1006, the transmitting operation 820 may include transmitting the one or more signals to the one or more sources of sterilizing radiation instructing the one or more sources of sterilizing radiation to emit sterilizing radiation as ultraviolet light. In some embodiments, one or more transmitting units are used to transmit one or more signals to one or more sources of sterilizing radiation. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1008, the transmitting operation 820 may include transmitting the one or more signals to the one or more sources of sterilizing radiation instructing the one or more sources of sterilizing radiation to emit sterilizing radiation as ultraviolet light having a wavelength between 100 and 400 nanometers. In some embodiments, one or more transmitting units are used to transmit one or more signals to one or more sources of sterilizing radiation to instruct the one or more sources of sterilizing radiation to emit sterilizing radiation as ultraviolet light having a wavelength between 100 and 400 nanometers. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1010, the transmitting operation 820 may include transmitting the one or more signals to the one or more sources of sterilizing radiation instructing the one or more sources of sterilizing radiation to emit sterilizing radiation as ultraviolet light having a wavelength between 180 and 300 nanometers. In some embodiments, one or more transmitting units are used to transmit one or more signals to one or more sources of sterilizing radiation to instruct the one or more sources of sterilizing radiation to emit sterilizing radiation as ultraviolet light having a wavelength between 180 and 300 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

Figure 11:
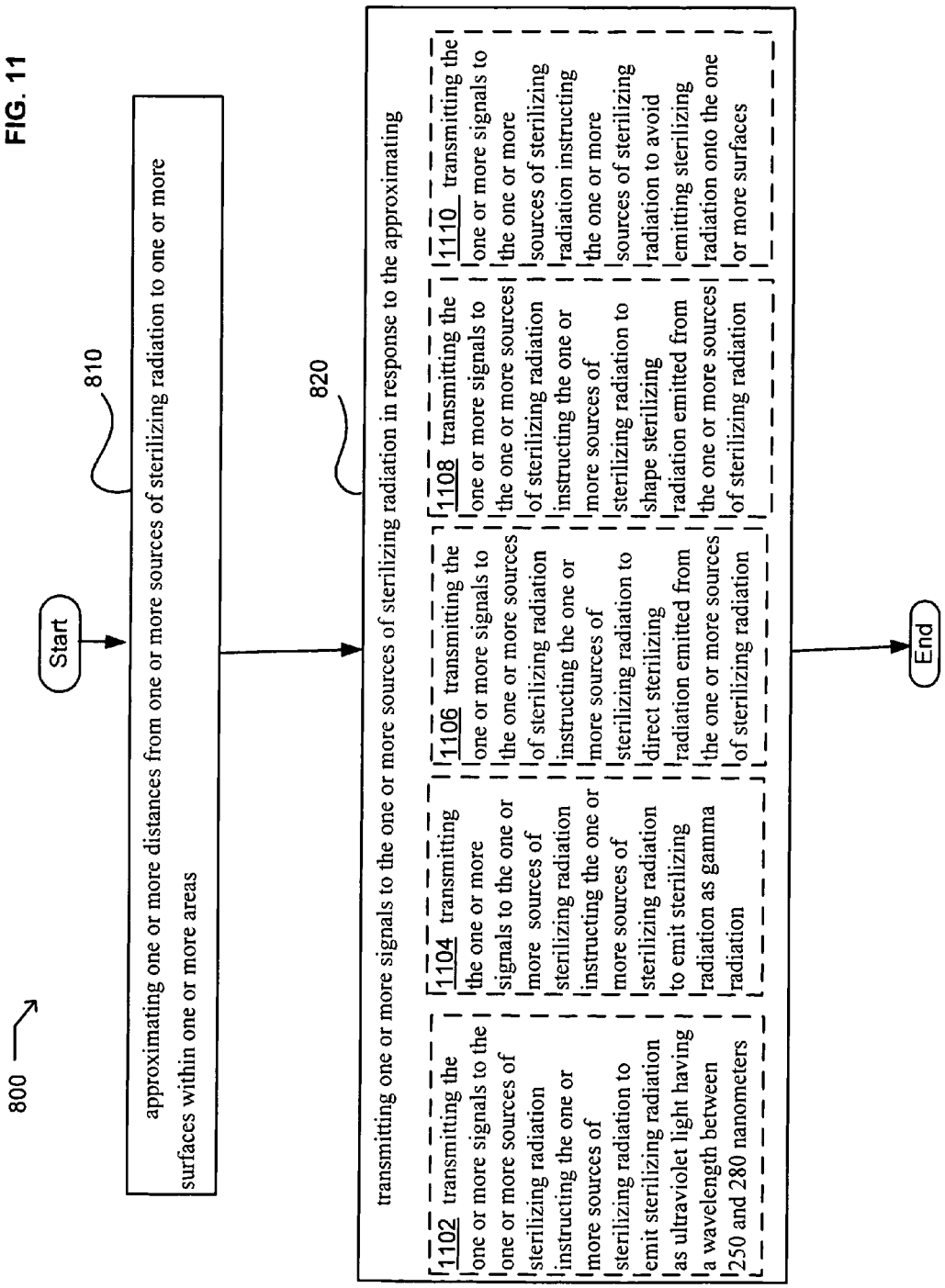
FIG. 11 illustrates an alternative embodiment of the example operation flow of FIG. 8.

FIG. 11 illustrates alternative embodiments of the example operational flow 800 of FIG. 8. FIG. 11 illustrates example embodiments where the transmitting operation 820 may include at least one additional operation. Additional operations may include an operation 1102, an operation 1104, an operation 1106, an operation 1108, and/or an operation 1110.

At operation 1102, the transmitting operation 820 may include transmitting the one or more signals to the one or more sources of sterilizing radiation instructing the one or more sources of sterilizing radiation to emit sterilizing radiation as ultraviolet light having a wavelength between 250 and 280 nanometers. In some embodiments, one or more transmitting units are used to transmit one or more signals to one or more sources of sterilizing radiation to instruct the one or more sources of sterilizing radiation to emit sterilizing radiation as ultraviolet light having a wavelength between 250 and 280 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1104, the transmitting operation 820 may include transmitting the one or more signals to the one or more sources of sterilizing radiation instructing the one or more sources of sterilizing radiation to emit sterilizing radiation as gamma radiation. In some embodiments, one or more transmitting units are used to transmit one or more signals to one or more sources of sterilizing radiation. Gamma radiation may be emitted from a source of sterilizing radiation that includes Cobalt-60. Such sources are known and are commercially available (MDS Nordion, Ottawa, Ontario, Canada).

At operation 1106, the transmitting operation 820 may include transmitting the one or more signals to the one or more sources of sterilizing radiation instructing the one or more sources of sterilizing radiation to direct sterilizing radiation emitted from the one or more sources of sterilizing radiation. In some embodiments, one or more transmitting units are used to transmit one or more signals to one or more sources of sterilizing radiation to direct sterilizing radiation emitted from the one or more sources of sterilizing radiation. In some embodiments, the sterilizing radiation is directed such that it impinges on a portion of an area. In some embodiments, the sterilizing radiation is directed away from one or more objects or surfaces. In some embodiments, the sterilizing radiation is focused such that it impinges on one or more defined surfaces or objects. Focusing of sterilizing radiation can serve to increase the intensity of sterilizing radiation impinging on a given area. Accordingly, sterilizing radiation may be intensified on an area or portion of an area in need of such treatment.

At operation 1108, the transmitting operation 820 may include transmitting the one or more signals to the one or more sources of sterilizing radiation instructing the one or more sources of sterilizing radiation to shape sterilizing radiation emitted from the one or more sources of sterilizing radiation. In some embodiments, one or more transmitting units are used to transmit one or more signals to one or more sources of sterilizing radiation to shape sterilizing radiation emitted from the one or more sources of sterilizing radiation. Sterilizing radiation may be shaped though use of numerous methods. For example, lenses and mirrors can be used to shape sterilizing radiation. Accordingly, the spatial distribution of sterilizing radiation can be controlled. In some embodiments, the sterilizing radiation is shaped such that one or more specific areas or objects are irradiated. In some embodiments, the sterilizing radiation is shaped to avoid irradiating one or more specific areas or objects. In some embodiments, the sterilization radiation is shaped into a beam that can be swept to sterilize one or more areas or one or more portions of one or more areas.

At operation 1110, the transmitting operation 820 may include transmitting the one or more signals to the one or more sources of sterilizing radiation instructing the one or more sources of sterilizing radiation to avoid emitting sterilizing radiation onto the one or more surfaces. In some embodiments, one or more transmitting units are used to transmit one or more signals to one or more sources of sterilizing radiation to avoid emitting sterilizing radiation onto the one or more objects. Numerous objects may be present or absent within one or more areas or one or more portions of one or more areas. Examples of such objects include, but are not limited to, humans, non-human animals, plants, surgical instruments, cooking utensils, eating utensils, sinks, tables, machinery, waste areas, and the like.

Figure 12:
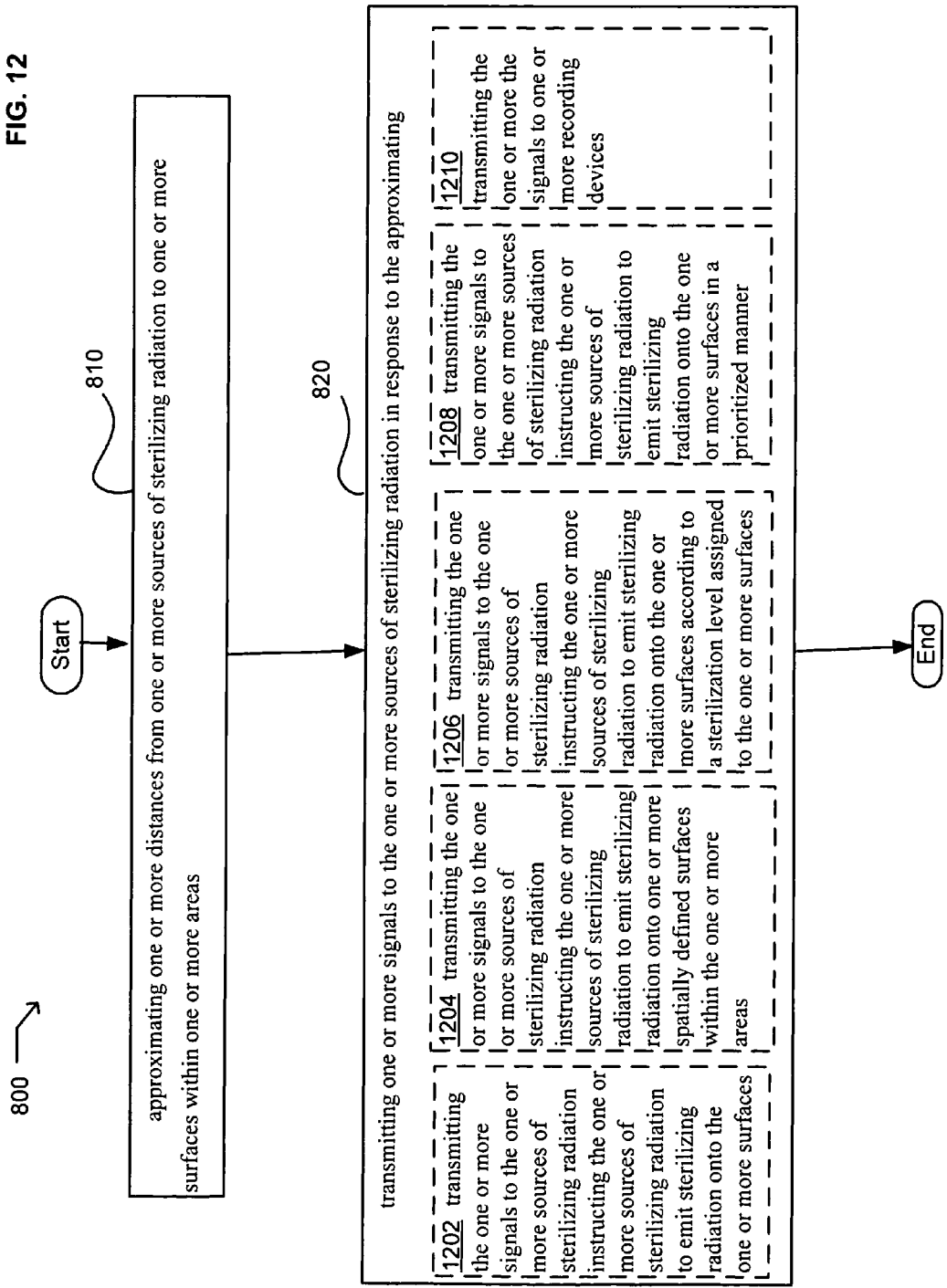
FIG. 12 illustrates an alternative embodiment of the example operation flow of FIG. 8.

FIG. 12 illustrates alternative embodiments of the example operational flow 800 of FIG. 8. FIG. 12 illustrates example embodiments where the transmitting operation 820 may include at least one additional operation. Additional operations may include an operation 1202, an operation 1204, an operation 1206, an operation 1208, and/or an operation 1210.

At operation 1202, the transmitting operation 820 may include transmitting the one or more signals to the one or more sources of sterilizing radiation instructing the one or more sources of sterilizing radiation to emit sterilizing radiation onto the one or more surfaces. In some embodiments, one or more transmitting units are used to transmit one or more signals to one or more sources of sterilizing radiation instructing the one or more sources of sterilizing radiation to emit sterilizing radiation onto the one or more surfaces. Examples of such surfaces may occur in areas that include, but are not limited to, hospitals, such as operating rooms and wards; transportation, such as airplanes, trains, cars, subways, buses; kitchens; bathrooms; and the like. Examples of surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 1204, the transmitting operation 820 may include transmitting the one or more signals to the one or more sources of sterilizing radiation instructing the one or more sources of sterilizing radiation to emit sterilizing radiation onto one or more spatially defined surfaces within the one or more areas. In some embodiments, one or more transmitting units are used to transmit one or more signals to one or more sources of sterilizing radiation to instruct the one or more sources of sterilizing radiation to emit sterilizing radiation onto one or more spatially defined surfaces within the one or more areas. Examples of such surfaces may occur in areas that include, but are not limited to, hospitals, such as operating rooms and wards; transportation, such as airplanes, trains, cars, subways, buses; kitchens; bathrooms; and the like. Examples of spatially defined surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 1206, the transmitting operation 820 may include transmitting the one or more signals to the one or more sources of sterilizing radiation instructing the one or more sources of sterilizing radiation to emit sterilizing radiation onto one or more surfaces according to a sterilization level assigned to the one or more surfaces. In some embodiments, one or more transmitting units are used to transmit one or more signals to one or more sources of sterilizing radiation instructing the one or more sources of sterilizing radiation to emit sterilizing radiation onto one or more surfaces according to a sterilization level assigned to the one or more surfaces. One or more sterilization levels may be assigned to one or more areas according to the degree of sterility desired for the one or more areas. For example, an operating room in a hospital may receive a high sterilization level while a reception room may receive a low sterilization level.

At operation 1208, the transmitting operation 820 may include transmitting the one or more signals to the one or more sources of sterilizing radiation instructing the one or more sources of sterilizing radiation to emit sterilizing radiation onto one or more surfaces in a prioritized manner. In some embodiments, one or more transmitting units are used to transmit one or more signals to one or more sources of sterilizing radiation instructing the one or more sources of sterilizing radiation to emit sterilizing radiation onto one or more surfaces in a prioritized manner. In some embodiments, a prioritized manner includes irradiating one or more surfaces with respect to immediacy, latency, intensity, and the like. In some embodiments, a prioritized manner includes irradiating one or more surfaces with regard to time-integrated intensity of sterilizing radiation such as irradiation of one or more surfaces as functions of either relative or absolute locations in the reference enclosed volume so that high-patient-hazard or high-infectivity-likelihood surfaces can be specified for the most rigorous and/or frequent irradiation.

At operation 1210, the transmitting operation 820 may include transmitting the one or more signals to one or more recording devices. In some embodiments, one or more transmitting units are used to transmit one or more signals to one or more recording devices. Many types of recording devices may be used. Examples of such recording devices include, but are not limited to, many types of memory, optical disks, magnetic disks, magnetic tape, and the like. In some embodiments, one or more recording devices provide for user interaction.

Figure 13:
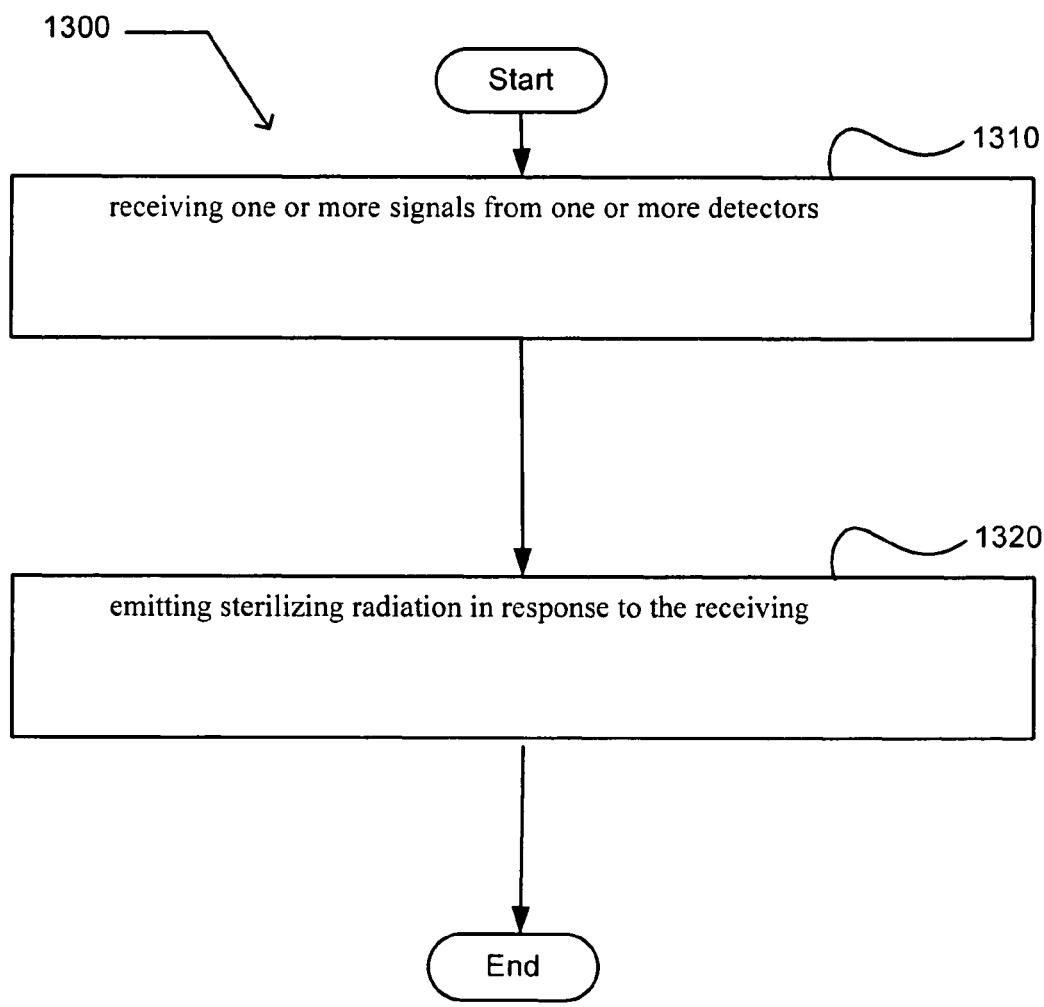
FIG. 13 illustrates an operational flow representing example operations related to sterilization methods.

FIG. 13 illustrates an operational flow 1300 representing examples of operations that are related to the performance of a sterilization method. In FIG. 13 and in following figures that include various examples of operations used during performance of the sterilization method, discussion and explanation may be provided with respect to the above-described example of FIG. 1C, and/or with respect to other examples and contexts. However, it should be understood that the operations may be executed in a number of other environments and contexts, and/or modified versions of FIG. 1C. Also, although the various operations are presented in the sequence(s) illustrated, it should be understood that the various operations may be performed in other orders than those which are illustrated, or may be performed concurrently.

After a start operation, the operational flow 1300 includes a receiving operation 1310 involving receiving one or more signals from one or more detectors. In some embodiments, one or more receiving units act to receive one or more signals from one or more detectors. In some embodiments, a single receiving unit acts to receive one or more signals from one or more detectors. In some embodiments, two or more receiving units act to receive one or more signals from one or more detectors. In some embodiments, two or more receiving units act to receive one or more signals from one or more detectors.

The operational flow 1300 also includes an emitting operation 1320 involving emitting sterilizing radiation in response to the receiving. In some embodiments, one or more sources of sterilizing radiation emit sterilizing radiation in response to the receiving. Accordingly, in some embodiments, a single source of sterilizing radiation or numerous sources of sterilizing radiation can respond to one receiving unit. In some embodiments, one source of sterilizing radiation can respond to one or more receiving units. In some embodiments, one or more sources of sterilizing radiation can respond to one or more receiving units.

Figure 14:
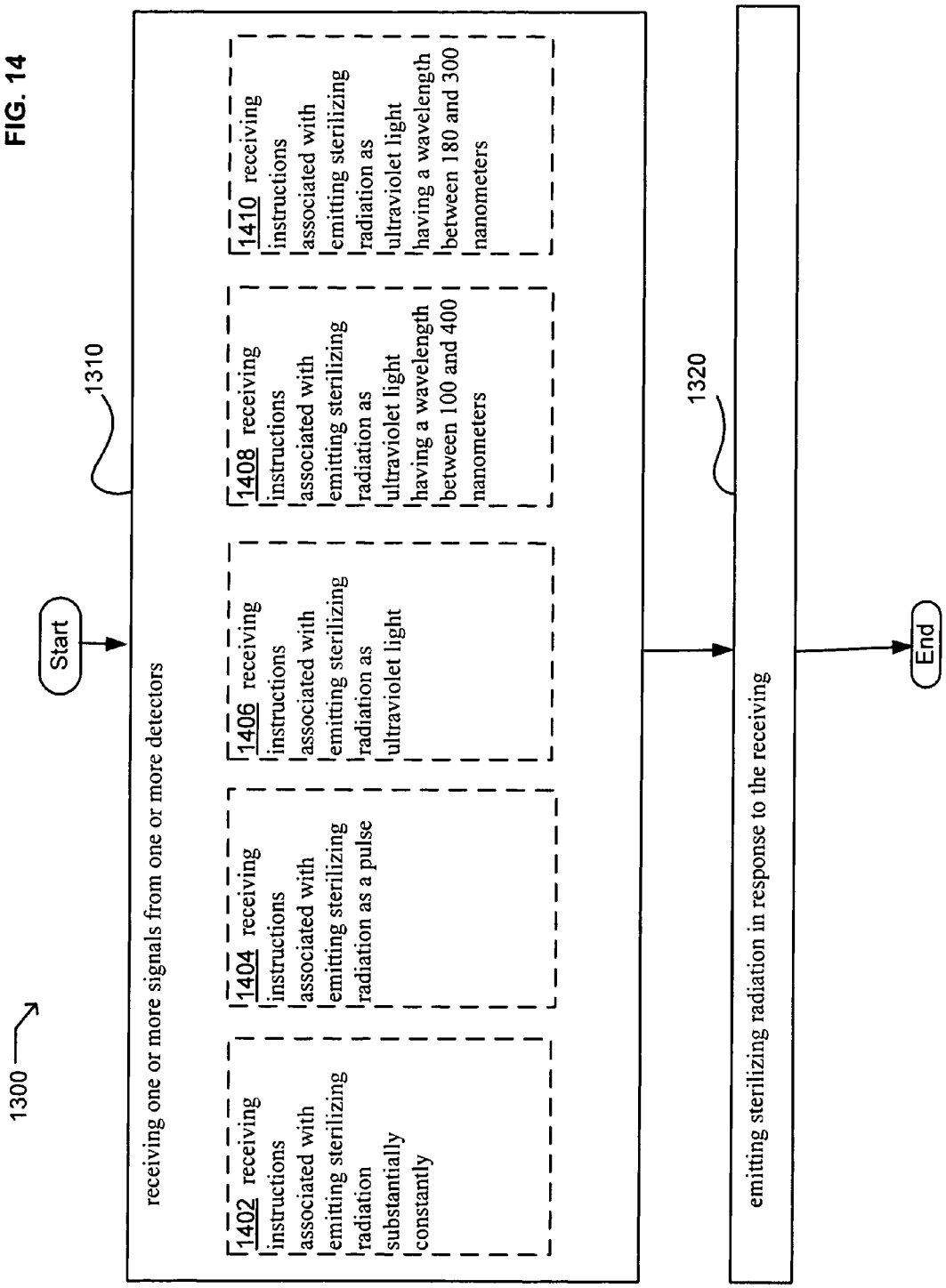
FIG. 14 illustrates an alternative embodiment of the example operation flow of FIG. 13.

FIG. 14 illustrates alternative embodiments of the example operational flow 1300 of FIG. 13. FIG. 14 illustrates example embodiments where the receiving operation 1310 may include at least one additional operation. Additional operations may include an operation 1402, an operation 1404, an operation 1406, an operation 1408, and/or an operation 1410.

At operation 1402, the receiving operation 1310 may include receiving instructions associated with emitting sterilizing radiation substantially constantly. In some embodiments, one or more receiving units are used to receive one or more signals from one or more detectors. In some embodiments, one or more receiving units receive instructions associated with emitting sterilizing radiation substantially constantly. In such instances, radiation will be emitted from one or more sources of sterilizing radiation in a manner that does not involve the alternating emission and non-emission of radiation according to a substantially cyclic pattern. However, such emission may be started and stopped, intensity modulated, paused, initiated, interrupted, resumed, programmed to follow a preprogrammed schedule, routine or sequence, or substantially any combination thereof. In contrast to constant emission, radiation emitted in a pulsed manner involves emission and non-emission of radiation according to a substantially cyclic repeated pattern.

At operation 1404, the receiving operation 1310 may include receiving instructions associated with emitting sterilizing radiation as a pulse. In some embodiments, one or more receiving units are used to receive one or more signals from one or more detectors. In some embodiments, one or more receiving units receive instructions associated with emitting sterilizing radiation as a pulse. In such instances, radiation will be emitted from the one or more sources of sterilizing radiation according to a substantially cyclic program that includes an alternating period of emission followed by a period of non-emission. For example, radiation is emitted in flashes that occur at specifically spaced time points. Emission of radiation that is emitted as a pulse may be started and stopped, intensity modulated, paused, initiated, interrupted, resumed, programmed to follow a preprogrammed schedule, routine or sequence, and substantially any combination thereof. In some embodiments, emission of radiation in a pulsed manner may be used to reduce heat output associated with a source of sterilizing radiation.

At operation 1406, the receiving operation 1310 may include receiving instructions associated with emitting sterilizing radiation as ultraviolet light. In some embodiments, one or more receiving units are used to receive one or more signals from one or more detectors. In some embodiments, one or more receiving units receive instructions associated with emitting sterilizing radiation as ultraviolet light. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1408, the receiving operation 1310 may include receiving instructions associated with emitting sterilizing radiation as ultraviolet light having a wavelength between 100 and 400 nanometers. In some embodiments, one or more receiving units are used to receive one or more signals from one or more detectors. In some embodiments, one or more receiving units receive instructions associated with emitting sterilizing radiation as ultraviolet light having a wavelength between 100 and 400 nanometers. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1410, the receiving operation 1310 may include receiving instructions associated with emitting sterilizing radiation as ultraviolet light having a wavelength between 180 and 300 nanometers. In some embodiments, one or more receiving units are used to receive one or more signals from one or more detectors. In some embodiments, one or more receiving units receive instructions associated with emitting sterilizing radiation as ultraviolet light having a wavelength between 180 and 300 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

Figure 15:
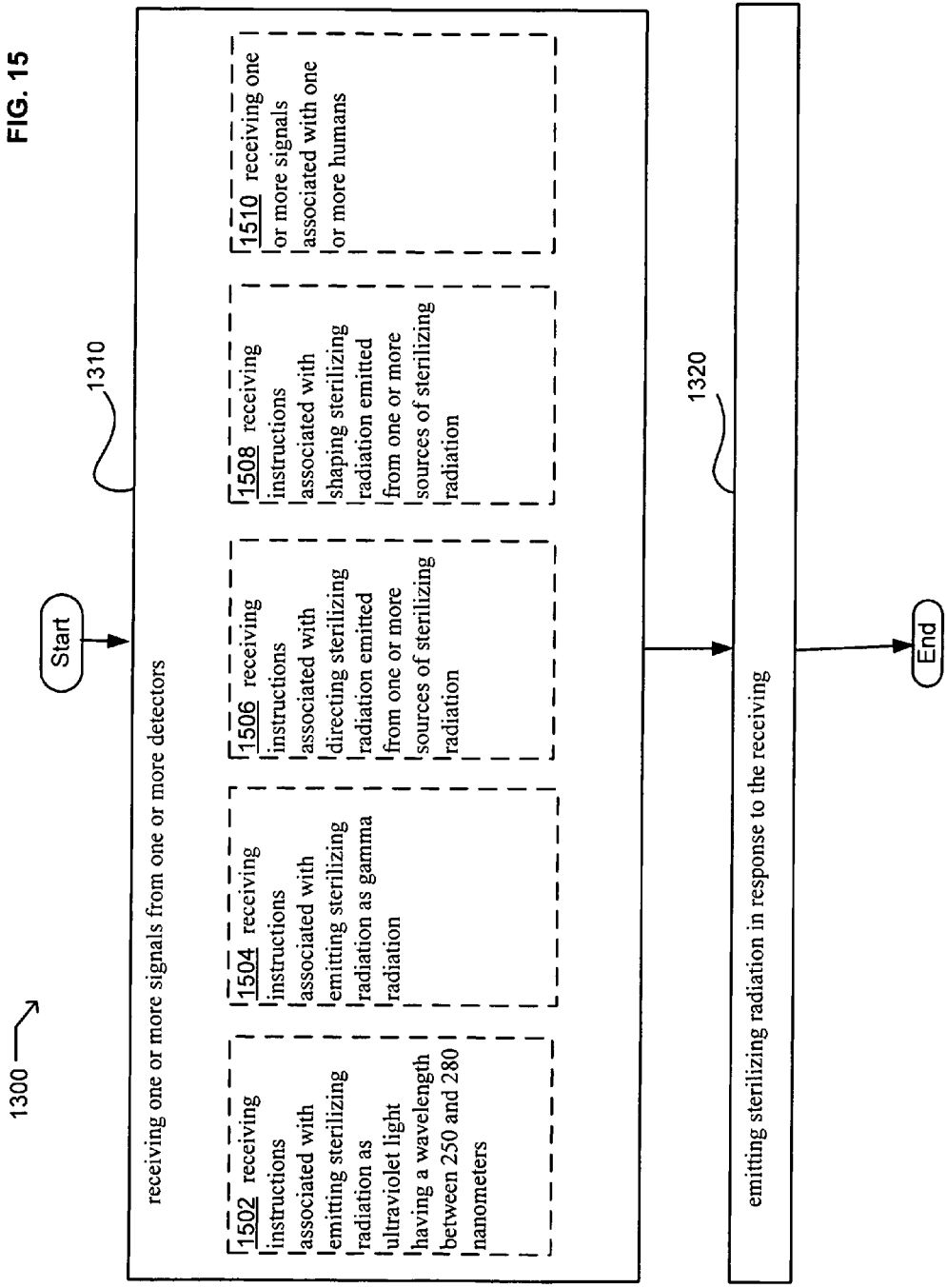
FIG. 15 illustrates an alternative embodiment of the example operation flow of FIG. 13.

FIG. 15 illustrates alternative embodiments of the example operational flow 1300 of FIG. 13. FIG. 15 illustrates example embodiments where the receiving operation 1310 may include at least one additional operation. Additional operations may include an operation 1502, an operation 1504, an operation 1506, an operation 1508, and/or an operation 1510.

At operation 1502, the receiving operation 1310 may include receiving instructions associated with emitting sterilizing radiation as ultraviolet light having a wavelength between 250 and 280 nanometers. In some embodiments, one or more receiving units are used to receive one or more signals from one or more detectors. In some embodiments, one or more receiving units receive instructions associated with emitting sterilizing radiation as ultraviolet light having a wavelength between 250 and 280 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1504, the receiving operation 1310 may include receiving instructions associated with emitting sterilizing radiation as gamma radiation. In some embodiments, one or more receiving units are used to receive one or more signals from one or more detectors. In some embodiments, one or more receiving units receive instructions associated with emitting sterilizing radiation as gamma radiation. Gamma radiation may be emitted from a source of sterilizing radiation that includes Cobalt-60. Such sources are known and are commercially available (MDS Nordion, Ottawa, Ontario, Canada).

At operation 1506, the receiving operation 1310 may include receiving instructions associated with directing sterilizing radiation emitted from one or more sources of sterilizing radiation. In some embodiments, one or more receiving units are used to receive one or more signals from one or more detectors. In some embodiments, one or more receiving units receive instructions associated with directing sterilizing radiation emitted from one or more sources of sterilizing radiation. In some embodiments, the sterilizing radiation is directed such that it impinges on a portion of an area. In some embodiments, the sterilizing radiation is directed away from one or more objects or surfaces. In some embodiments, the sterilizing radiation is focused such that it impinges on one or more defined surfaces or objects. Focusing of sterilizing radiation can serve to increase the intensity of sterilizing radiation impinging on a given area. Accordingly, sterilizing radiation may be intensified on an area or portion of an area in need of such treatment.

At operation 1508, the receiving operation 1310 may include receiving instructions associated with shaping sterilizing radiation emitted from one or more sources of sterilizing radiation. In some embodiments, one or more receiving units are used to receive one or more signals from one or more detectors. In some embodiments, one or more receiving units receive instructions associated with shaping sterilizing radiation emitted from one or more sources of sterilizing radiation. Sterilizing radiation may be shaped though use of numerous methods. For example, lenses and mirrors can be used to shape sterilizing radiation. Accordingly, the spatial distribution of sterilizing radiation can be controlled. In some embodiments, the sterilizing radiation is shaped such that one or more specific areas or objects are irradiated. In some embodiments, the sterilizing radiation is shaped to avoid irradiating one or more specific areas or objects. In some embodiments, the sterilization radiation is shaped into a beam that can be swept to sterilize one or more areas or one or more portions of one or more areas.

At operation 1510, the receiving operation 1310 may include receiving one or more signals associated with one or more humans. In some embodiments, one or more receiving units are used to receive one or more signals from one or more detectors. In some embodiments, one or more receiving units receive one or more signals associated with one or more humans. In some embodiments, one signal associated with a human can be received. In some embodiments, one or more signals associated with a human can be received. In some embodiments, one or more signals associated with one or more humans can be received. In other embodiments, receiving one or more signals associated with one or more humans includes receiving the absence of any signal associated with one or more humans. Numerous signals that are associated with one or more humans can be received. Examples of such signals include, but are not limited to, infrared radiation, retinal reflection, motion detection, profile detection, and substantially any combination thereof. In some embodiments, receiving one or more signals associated with one or more humans includes receiving one or more signals associated with one or more tags that are attached to one or more humans. In other embodiments, receiving one or more signals associated with one or more humans includes receiving one or more signals associated with one or more access devices that are used to enter one or more areas. Examples of access devices include, but are not limited to, access cards, key pads, locks, or other devices coupled to entry of one or more humans into one or more areas.

Figure 16:
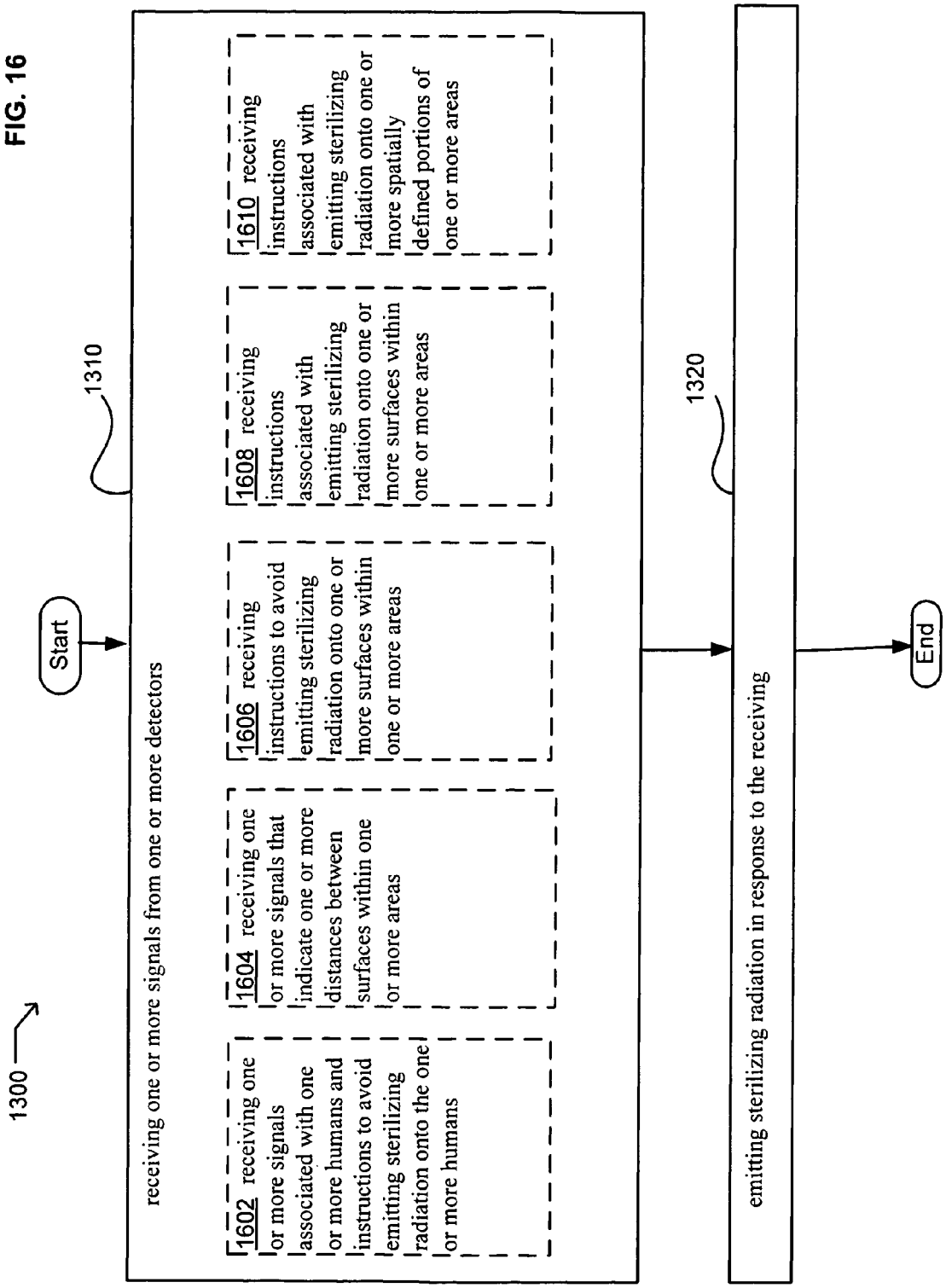
FIG. 16 illustrates an alternative embodiment of the example operation flow of FIG. 13.

FIG. 16 illustrates alternative embodiments of the example operational flow 1300 of FIG. 13. FIG. 16 illustrates example embodiments where the receiving operation 1310 may include at least one additional operation. Additional operations may include an operation 1602, an operation 1604, an operation 1606, an operation 1608, and/or an operation 1610.

At operation 1602, the receiving operation 1310 may include receiving one or more signals associated with one or more humans and instructions to avoid emitting sterilizing radiation onto the one or more humans. In some embodiments, one or more receiving units are used to receive one or more signals from one or more detectors. In some embodiments, one or more receiving units receive one or more signals associated with one or more humans and instructions to avoid emitting sterilizing radiation onto the one or more humans. In some embodiments, one signal associated with a human can be received. In some embodiments, one or more signals associated with a human can be received. In some embodiments, one or more signals associated with one or more humans can be received. In other embodiments, receiving one or more signals associated with one or more humans includes receiving the absence of any signal associated with one or more humans. Numerous signals that are associated with one or more humans can be received. Examples of such signals include, but are not limited to, infrared radiation, retinal reflection, motion detection, profile detection, and substantially any combination thereof. In some embodiments, receiving one or more signals associated with one or more humans includes receiving one or more signals associated with one or more tags that are attached to one or more humans. In other embodiments, receiving one or more signals associated with one or more humans includes receiving one or more signals associated with one or more access devices that are used to enter one or more areas. Examples of access devices include, but are not limited to, access cards, key pads, locks, or other devices coupled to entry of one or more humans into one or more areas. In some embodiments, the instructions to avoid emitting sterilizing radiation onto the one or more humans includes instructions to direct the sterilizing radiation away from the one or more humans. In some embodiments, the instructions to avoid emitting sterilizing radiation onto the one or more humans includes instructions to discontinue emission of sterilizing radiation from one or more sources of sterilizing radiation. In some embodiments, the instructions to avoid emitting sterilizing radiation onto the one or more humans includes instructions to not start emitting sterilizing radiation from one or more sources of sterilizing radiation.

At operation 1604, the receiving operation 1310 may include receiving one or more signals that indicate one or more distances between surfaces within one or more areas. In some embodiments, one or more receiving units are used to receive one or more signals from one or more detectors. In some embodiments, one or more receiving units receive one or more signals that indicate one or more distances between surfaces within one or more areas. In some embodiments, the one or more signals indicate approximate distances between one or more surfaces within one or more areas. In some embodiments, the one or more signals indicate approximate distances between one or more surfaces in one or more areas and one or more sources of sterilizing radiation. In some embodiments, the one or more surfaces are on one or more objects included within the one or more areas. In some embodiments, the one or more surfaces are on one or more humans.

At operation 1606, the receiving operation 1310 may include receiving instructions to avoid emitting sterilizing radiation onto one or more surfaces within one or more areas. In some embodiments, one or more receiving units are used to receive one or more signals from one or more detectors. In some embodiments, one or more receiving units receive instructions to avoid emitting sterilizing radiation onto one or more surfaces within one or more areas. Examples of such areas include, but are not limited to, hospitals, such as operating rooms and wards; transportation, such as airplanes, trains, cars, subways, buses; kitchens; bathrooms; and the like. Examples of surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 1608, the receiving operation 1310 may include receiving instructions associated with emitting sterilizing radiation onto one or more surfaces within one or more areas. In some embodiments, one or more receiving units are used to receive one or more signals from one or more detectors. In some embodiments, one or more receiving units receive instructions associated with emitting sterilizing radiation onto one or more surfaces within one or more areas. Examples of such areas include, but are not limited to, hospitals, such as operating rooms and wards; transportation, such as airplanes, trains, cars, subways, buses; kitchens; bathrooms; and the like. Examples of surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 1610, the receiving operation 1310 may include receiving instructions associated with emitting sterilizing radiation onto one or more spatially defined portions of one or more areas. In some embodiments, one or more receiving units are used to receive one or more signals from one or more detectors. In some embodiments, one or more receiving units receive instructions associated with emitting sterilizing radiation onto one or more spatially defined portions of one or more areas. Examples of such areas include, but are not limited to, hospitals, such as operating rooms and wards; transportation, such as airplanes, trains, cars, subways, buses; kitchens; bathrooms; and the like. Examples of spatially defined portions of one or more areas include, but are not limited to, one or more sinks within one or more operating rooms, one or more tables within one or more operating rooms, one or more portions of flooring within one or more operating rooms, one or more portions of siding within one or more operating rooms, and the like.

Figure 17:
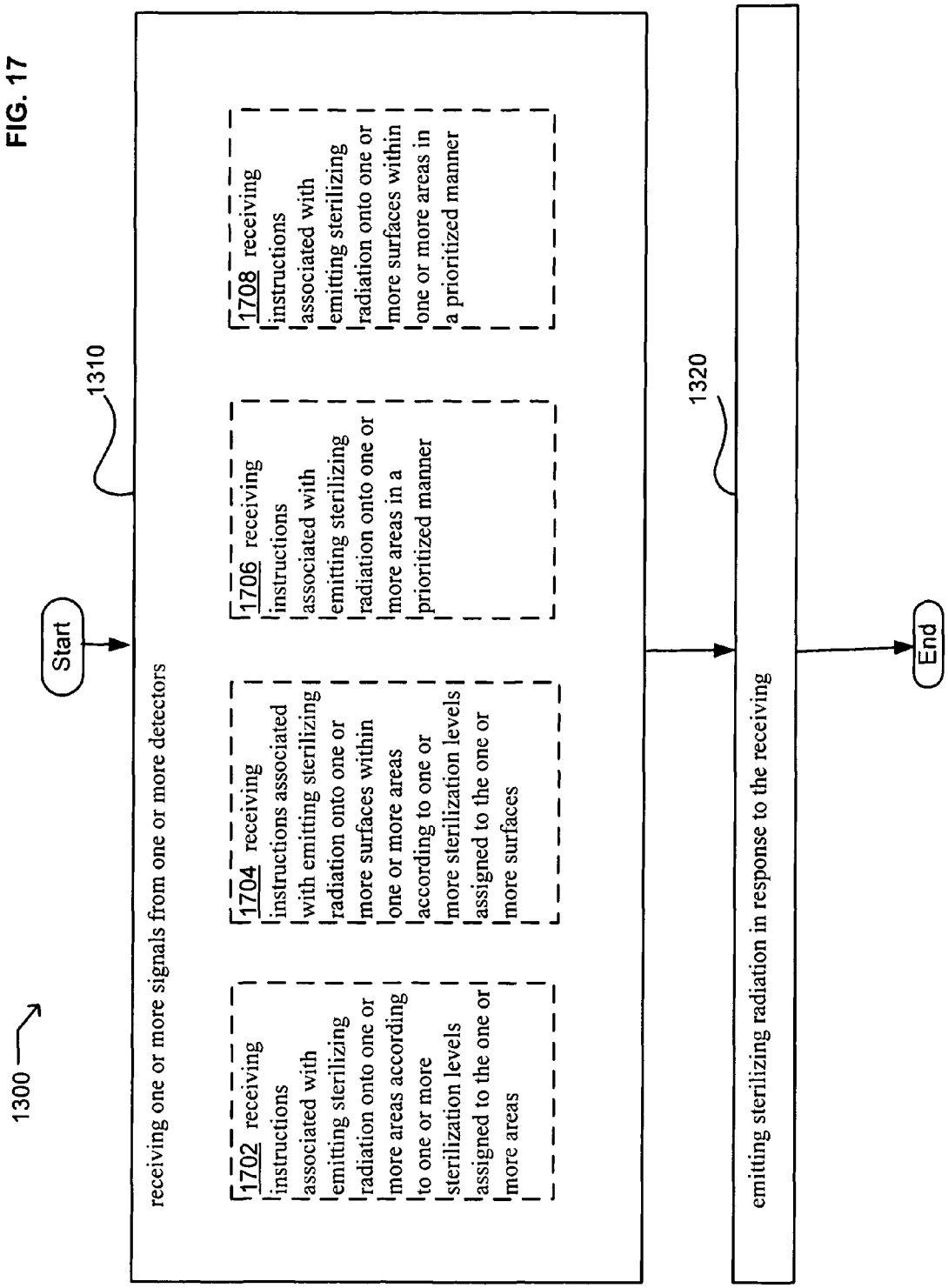
FIG. 17 illustrates an alternative embodiment of the example operation flow of FIG. 13.

FIG. 17 illustrates alternative embodiments of the example operational flow 1300 of FIG. 13. FIG. 17 illustrates example embodiments where the receiving operation 1310 may include at least one additional operation. Additional operations may include an operation 1702, an operation 1704, an operation 1706, and/or an operation 1708.

At operation 1702, the receiving operation 1310 may include receiving instructions associated with emitting sterilizing radiation onto one or more areas according to one or more sterilization levels assigned to the one or more areas. In some embodiments, one or more receiving units are used to receive one or more signals from one or more detectors. In some embodiments, one or more receiving units receive instructions associated with emitting sterilizing radiation onto one or more areas according to one or more sterilization levels assigned to the one or more areas. One or more sterilization levels may be assigned to one or more areas according to the degree of sterility desired for the one or more areas. For example, an operating room in a hospital may receive a high sterilization level while a reception room may receive a low sterilization level.

At operation 1704, the receiving operation 1310 may include receiving instructions associated with emitting sterilizing radiation onto one or more surfaces within one or more areas according to one or more sterilization levels assigned to the one or more surfaces. In some embodiments, one or more receiving units are used to receive one or more signals from one or more detectors. In some embodiments, one or more receiving units receive instructions associated with emitting sterilizing radiation onto one or more surfaces within one or more areas according to one or more sterilization levels assigned to the one or more surfaces. One or more sterilization levels may be assigned to one or more surfaces within one or more areas according to the degree of sterility desired for the one or more areas. For example, a surface within an operating room in a hospital may receive a high sterilization level while a surface within a reception room may receive a low sterilization level.

At operation 1706, the receiving operation 1310 may include receiving instructions associated with emitting sterilizing radiation onto one or more areas in a prioritized manner. In some embodiments, one or more receiving units are used to receive one or more signals from one or more detectors. In some embodiments, one or more receiving units receive instructions associated with emitting sterilizing radiation onto one or more areas in a prioritized manner. In some embodiments, a prioritized manner includes irradiating one or more areas with respect to immediacy, latency, intensity, and the like. In some embodiments, a prioritized manner includes irradiating one or more areas with regard to time-integrated intensity of sterilizing radiation such as irradiation of one or more areas as functions of either relative or absolute locations in the reference enclosed volume so that high-patient-hazard or high-infectivity-likelihood areas and volumes can be specified for the most rigorous and/or frequent irradiation.

At operation 1708, the receiving operation 1310 may include receiving instructions associated with emitting sterilizing radiation onto one or more surfaces within one or more areas in a prioritized manner. In some embodiments, one or more receiving units are used to receive one or more signals from one or more detectors. In some embodiments, one or more receiving units receive instructions associated with emitting sterilizing radiation onto one or more surfaces within one or more areas in a prioritized manner. In some embodiments, a prioritized manner includes irradiating one or more surfaces with respect to immediacy, latency, intensity, and the like. In some embodiments, a prioritized manner includes irradiating one or more surfaces with regard to time-integrated intensity of sterilizing radiation such as irradiation of one or more surfaces as functions of either relative or absolute locations in the reference enclosed volume so that high-patient-hazard or high-infectivity-likelihood surfaces and volumes can be specified for the most rigorous and/or frequent irradiation.

Figure 18:
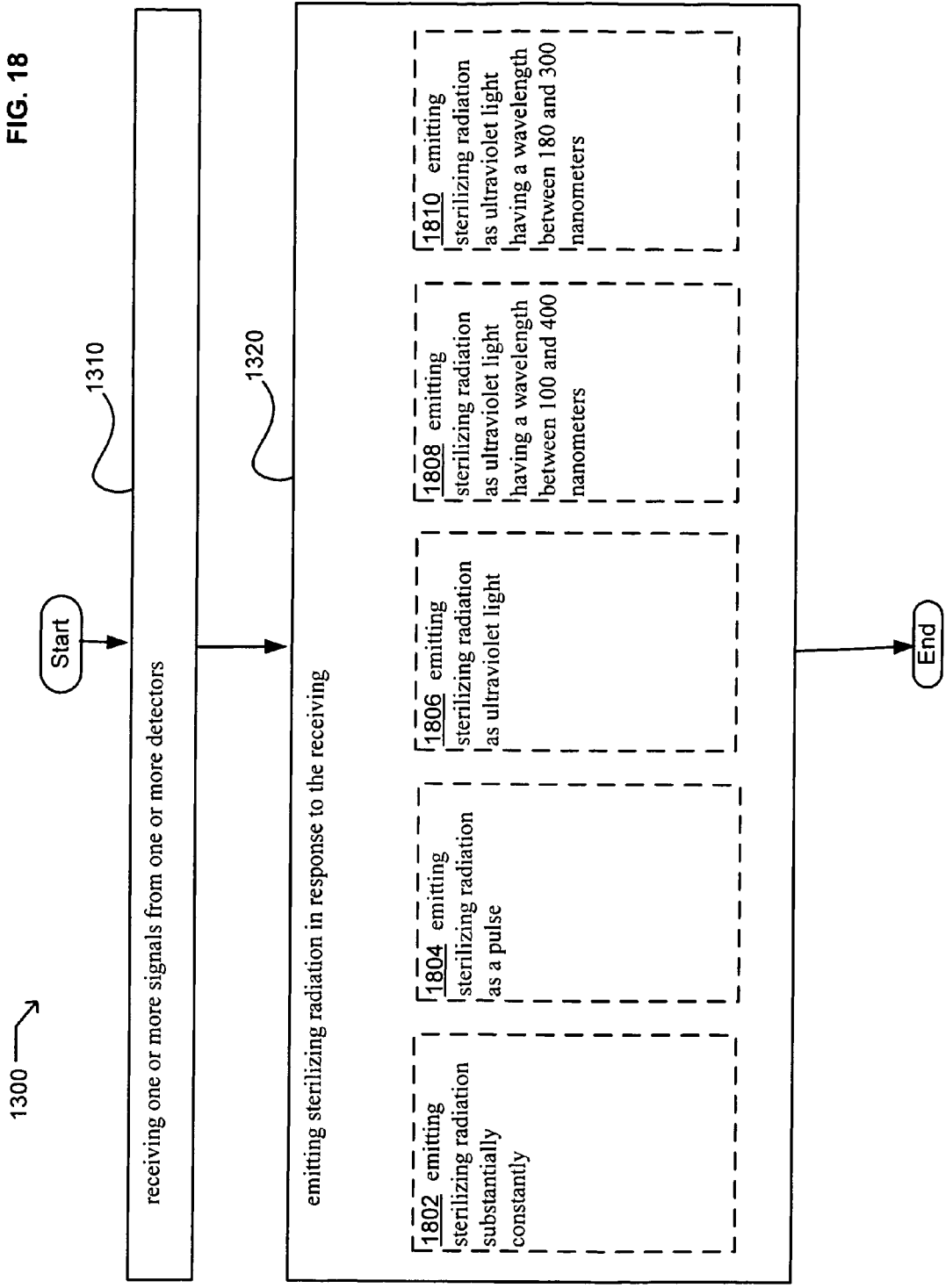
FIG. 18 illustrates an alternative embodiment of the example operation flow of FIG. 13.

FIG. 18 illustrates alternative embodiments of the example operational flow 1300 of FIG. 13. FIG. 18 illustrates example embodiments where the emitting operation 1320 may include at least one additional operation. Additional operations may include an operation 1802, an operation 1804, an operation 1806, an operation 1808, and/or an operation 1810.

At operation 1802, the emitting operation 1320 may include emitting sterilizing radiation substantially constantly. In some embodiments, one or more sources of sterilizing radiation emit sterilizing radiation in response to one or more receiving units. In some embodiments, one or more sources of sterilizing radiation may emit sterilizing radiation substantially constantly. In such instances, one or more sources of sterilizing radiation will emit radiation in a manner that does not involve the alternating emission and non-emission of radiation according to a substantially cyclic pattern. However, such emission may be started and stopped, intensity modulated, paused, initiated, interrupted, resumed, programmed to follow a preprogrammed schedule, routine or sequence, or substantially any combination thereof. In contrast to constant emission, radiation emitted in a pulsed manner involves emission and non-emission of radiation according to a substantially cyclic repeated pattern.

At operation 1804, the emitting operation 1320 may include emitting sterilizing radiation as a pulse. In some embodiments, one or more sources of sterilizing radiation emit sterilizing radiation in response to one or more receiving units. In some embodiments, one or more sources of sterilizing radiation may emit sterilizing radiation as a pulse. In such instances, radiation will be emitted from the one or more sources of sterilizing radiation according to a substantially cyclic program that includes an alternating period of emission followed by a period of non-emission. For example, radiation is emitted in flashes that occur at specifically spaced time points. Emission of radiation that is emitted as a pulse may be started and stopped, intensity modulated, paused, initiated, interrupted, resumed, programmed to follow a preprogrammed schedule, routine or sequence, and substantially any combination thereof. In some embodiments, emission of radiation in a pulsed manner may be used to reduce heat output associated with a source of sterilizing radiation.

At operation 1806, the emitting operation 1320 may include emitting sterilizing radiation as ultraviolet light. In some embodiments, one or more sources of sterilizing radiation emit sterilizing radiation in response to one or more receiving units. In some embodiments, one or more sources of sterilizing radiation may emit sterilizing radiation as ultraviolet light. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1808, the emitting operation 1320 may include emitting sterilizing radiation as ultraviolet light having a wavelength between 100 and 400 nanometers. In some embodiments, one or more sources of sterilizing radiation emit sterilizing radiation in response to one or more receiving units. In some embodiments, one or more sources of sterilizing radiation may emit sterilizing radiation as ultraviolet light having a wavelength between 100 and 400 nanometers. In some embodiments, numerous wavelengths of ultraviolet light can be emitted from a source of sterilizing radiation. In some embodiments, a source of sterilizing radiation can emit any wavelength of ultraviolet light that is between 100 nanometers and 400 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1810, the emitting operation 1320 may include emitting sterilizing radiation as ultraviolet light having a wavelength between 180 and 300 nanometers. In some embodiments, one or more sources of sterilizing radiation emit sterilizing radiation in response to one or more receiving units. In some embodiments, numerous wavelengths of ultraviolet light can be emitted from a source of sterilizing radiation. In some embodiments, one or more sources of sterilizing radiation may emit sterilizing radiation as ultraviolet light having a wavelength between 180 and 300 nanometers. In some embodiments, a source of sterilizing radiation can emit any wavelength of ultraviolet light that is between 180 nanometers and 300 nanometers. In some embodiments, a source of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

Figure 19:
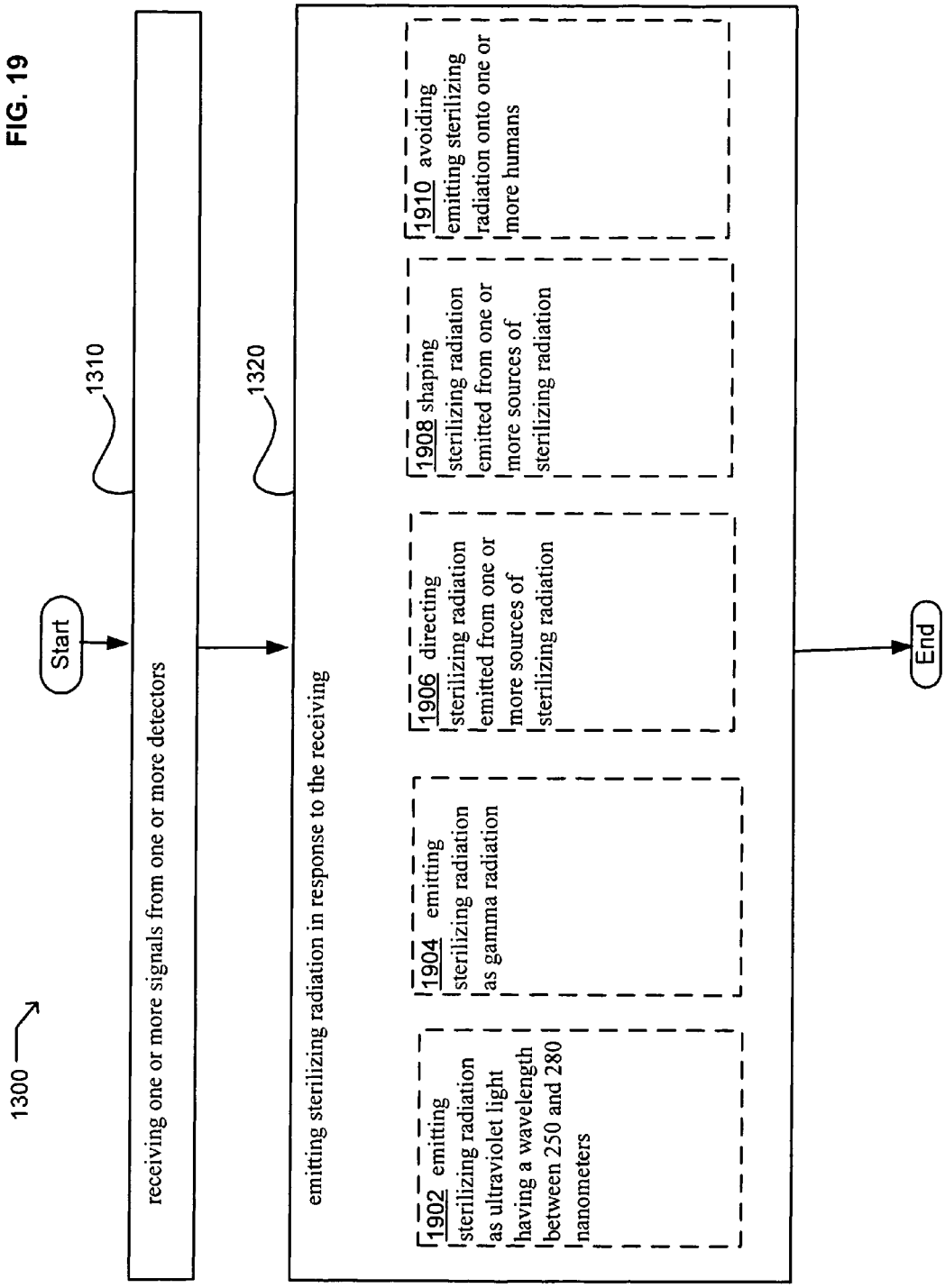
FIG. 19 illustrates an alternative embodiment of the example operation flow of FIG. 13.

FIG. 19 illustrates alternative embodiments of the example operational flow 1300 of FIG. 13. FIG. 19 illustrates example embodiments where the emitting operation 1320 may include at least one additional operation. Additional operations may include an operation 1902, an operation 1904, an operation 1906, an operation 1908, and/or an operation 1910.

At operation 1902, the emitting operation 1320 may include emitting sterilizing radiation as ultraviolet light having a wavelength between 250 and 280 nanometers. In some embodiments, one or more sources of sterilizing radiation emit sterilizing radiation in response to one or more receiving units. In some embodiments, numerous wavelengths of ultraviolet light can be emitted from a source of sterilizing radiation. In some embodiments, one or more sources of sterilizing radiation may emit sterilizing radiation as ultraviolet light having a wavelength between 250 and 280 nanometers. In some embodiments, one or more sources of sterilizing radiation can emit any wavelength of ultraviolet light that is between 255 nanometers and 280 nanometers. In some embodiments, a source of sterilizing radiation can emit any wavelength of ultraviolet light that is between 260 nanometers and 270 nanometers. In some embodiments, a source of sterilizing radiation can emit ultraviolet light at about 260 nanometers. In some embodiments, a source of sterilizing radiation can emit any wavelength of ultraviolet light that is centered but asymmetric on 265 nanometers. In addition, in some embodiments, a source of sterilizing radiation that emits ultraviolet light can also emit additional forms of radiation. These additional forms of radiation can include, but are not limited to, gamma radiation, visible light, infrared radiation, electron beams, and the like. Sources of ultraviolet radiation are commercially available (Enhance-It, LLC, Hilton Head Island, S.C. 29926 and Advanced Sterilization Products, Irvine, Calif. 92618).

At operation 1904, the emitting operation 1320 may include emitting sterilizing radiation as gamma radiation. In some embodiments, one or more sources of sterilizing radiation emit sterilizing radiation in response to one or more receiving units. In some embodiments, one or more sources of sterilizing radiation may emit sterilizing radiation as gamma radiation. Gamma radiation may be emitted from a source of sterilizing radiation that includes Cobalt-60. Such sources are known and are commercially available (MDS Nordion, Ottawa, Ontario, Canada).

At operation 1906, the emitting operation 1320 may include directing sterilizing radiation emitted from one or more sources of sterilizing radiation. In some embodiments, one or more sources of sterilizing radiation emit sterilizing radiation in response to one or more receiving units. In some embodiments, one or more sources of sterilizing radiation may direct sterilizing radiation emitted from the one or more sources of sterilizing radiation. In some embodiments, the sterilizing radiation is directed such that it impinges on a portion of an area. In some embodiments, the sterilizing radiation is directed away from one or more objects or surfaces. In some embodiments, the sterilizing radiation is focused such that it impinges on one or more defined surfaces or objects. Focusing of sterilizing radiation can serve to increase the intensity of sterilizing radiation impinging on a given area. Accordingly, sterilizing radiation may be intensified on an area or portion of an area in need of such treatment.

At operation 1908, the emitting operation 1320 may include shaping sterilizing radiation emitted from one or more sources of sterilizing radiation. In some embodiments, one or more sources of sterilizing radiation emit sterilizing radiation in response to one or more receiving units. In some embodiments, one or more sources of sterilizing radiation may shape sterilizing radiation emitted from the one or more sources of sterilizing radiation. Sterilizing radiation may be shaped though use of numerous methods. For example, lenses and mirrors can be used to shape sterilizing radiation. Accordingly, the spatial distribution of sterilizing radiation can be controlled. In some embodiments, the sterilizing radiation is shaped such that one or more specific areas or objects are irradiated. In some embodiments, the sterilizing radiation is shaped to avoid irradiating one or more specific areas or objects. In some embodiments, the sterilization radiation is shaped into a beam that can be swept to sterilize one or more areas or one or more portions of one or more areas.

At operation 1910, the emitting operation 1320 may include avoiding emitting sterilizing radiation onto one or more humans. In some embodiments, one or more sources of sterilizing radiation emit sterilizing radiation in response to one or more receiving units. In some embodiments, one or more sources of sterilizing radiation avoiding emitting sterilizing radiation onto one or more humans. In some embodiments, avoiding emitting sterilizing radiation onto one or more humans includes directing the sterilizing radiation away from the one or more humans. In some embodiments, avoiding emitting sterilizing radiation onto one or more humans includes instructions to discontinue emission of sterilizing radiation from one or more sources of sterilizing radiation. In some embodiments, avoiding emitting sterilizing radiation onto one or more humans includes instructions to not start emitting sterilizing radiation from one or more sources of sterilizing radiation.

Figure 20:
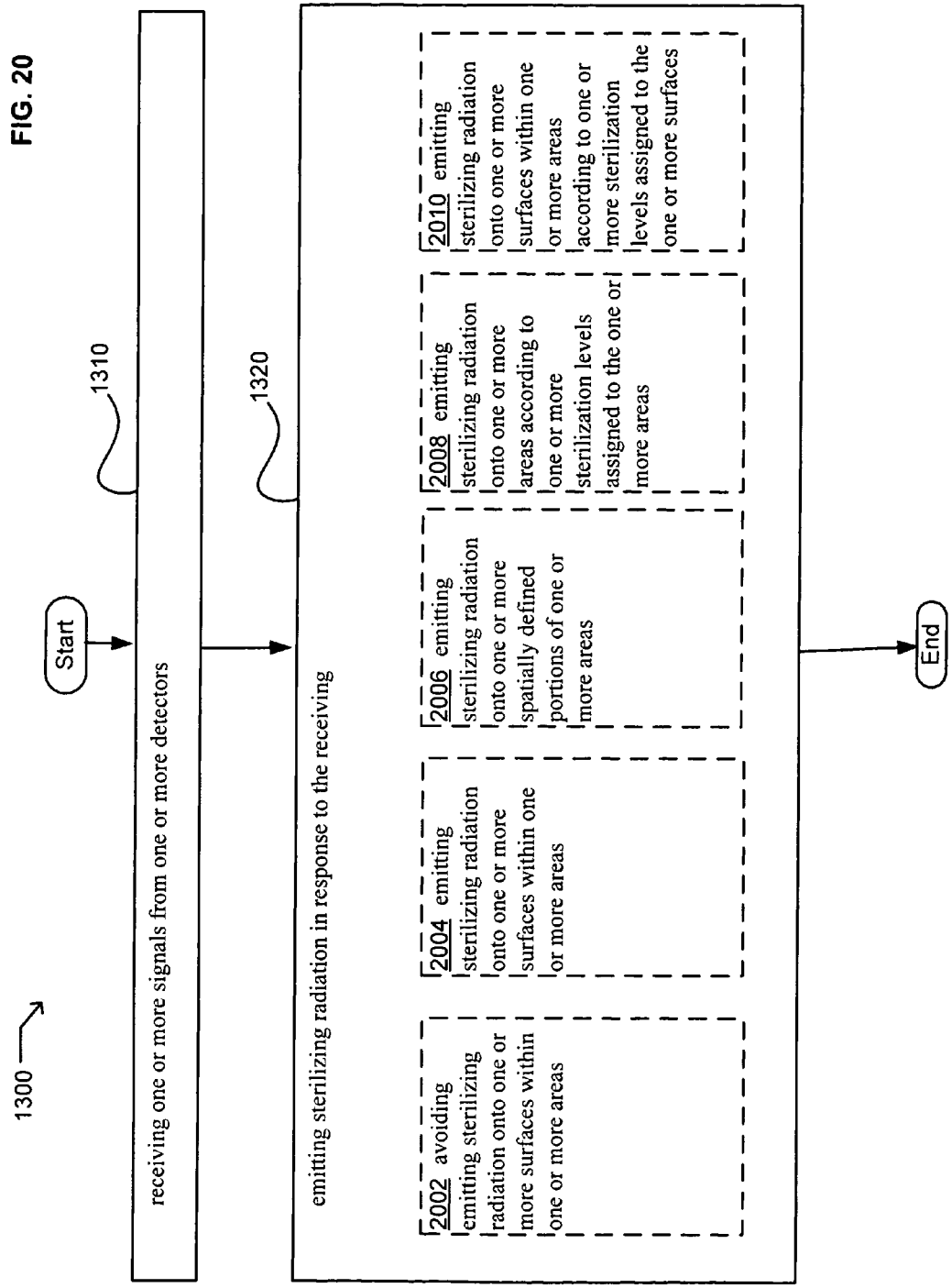
FIG. 20 illustrates an alternative embodiment of the example operation flow of FIG. 13.

FIG. 20 illustrates alternative embodiments of the example operational flow 1300 of FIG. 13. FIG. 20 illustrates example embodiments where the emitting operation 1320 may include at least one additional operation. Additional operations may include an operation 2002, an operation 2004, an operation 2006, an operation 2008, and/or an operation 2010.

At operation 2002, the emitting operation 1320 may include avoiding emitting sterilizing radiation onto one or more surfaces within one or more areas. In some embodiments, one or more sources of sterilizing radiation emit sterilizing radiation in response to one or more receiving units. In some embodiments, one or more sources of sterilizing radiation avoiding emitting sterilizing radiation onto one or more surfaces within one or more areas. Examples of such areas include, but are not limited to, hospitals, such as operating rooms and wards; transportation, such as airplanes, trains, cars, subways, buses; kitchens; bathrooms; and the like. Examples of surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 2004, the emitting operation 1320 may include emitting sterilizing radiation onto one or more surfaces within one or more areas. In some embodiments, one or more sources of sterilizing radiation emit sterilizing radiation in response to one or more receiving units. In some embodiments, one or more sources of sterilizing radiation emit sterilizing radiation onto one or more surfaces within one or more areas. Examples of such areas include, but are not limited to, hospitals, such as operating rooms and wards; transportation, such as airplanes, trains, cars, subways, buses; kitchens; bathrooms; and the like. Examples of surfaces within one or more areas include, but are not limited to, one or more sink surfaces within one or more operating rooms, one or more table surfaces within one or more operating rooms, one or more floor surfaces within one or more operating rooms, one or more siding surfaces within one or more operating rooms, and the like.

At operation 2006, the emitting operation 1320 may include emitting sterilizing radiation onto one or more spatially defined portions of one or more areas. In some embodiments, one or more sources of sterilizing radiation emit sterilizing radiation in response to one or more receiving units. In some embodiments, one or more sources of sterilizing radiation emit sterilizing radiation onto one or more spatially defined portions of one or more areas. Examples of such areas include, but are not limited to, hospitals, such as operating rooms and wards; transportation, such as airplanes, trains, cars, subways, buses; kitchens; bathrooms; and the like. Examples of spatially defined portions of one or more areas include, but are not limited to, one or more sinks within one or more operating rooms, one or more tables within one or more operating rooms, one or more portions of flooring within one or more operating rooms, one or more portions of siding within one or more operating rooms, and the like.

At operation 2008, the emitting operation 1320 may include emitting sterilizing radiation onto one or more areas according to one or more sterilization levels assigned to the one or more areas. In some embodiments, one or more sources of sterilizing radiation emit sterilizing radiation in response to one or more receiving units. In some embodiments, one or more sources of sterilizing radiation emit sterilizing radiation onto one or more areas according to one or more sterilization levels assigned to the one or more areas. One or more sterilization levels may be assigned to one or more areas according to the degree of sterility desired for the one or more areas. For example, an operating room in a hospital may receive a high sterilization level while a reception room may receive a low sterilization level.

At operation 2010, the emitting operation 1320 may include emitting sterilizing radiation onto one or more surfaces within one or more areas according to one or more sterilization levels assigned to the one or more surfaces. In some embodiments, one or more sources of sterilizing radiation emit sterilizing radiation in response to one or more receiving units. In some embodiments, one or more sources of sterilizing radiation emit sterilizing radiation onto one or more surfaces within one or more areas according to one or more sterilization levels assigned to the one or more surfaces. One or more sterilization levels may be assigned to one or more surfaces according to the degree of sterility desired for the one or more surfaces. For example, a surface within an operating room in a hospital may receive a high sterilization level while a surface within a reception room may receive a low sterilization level.

Figure 21:
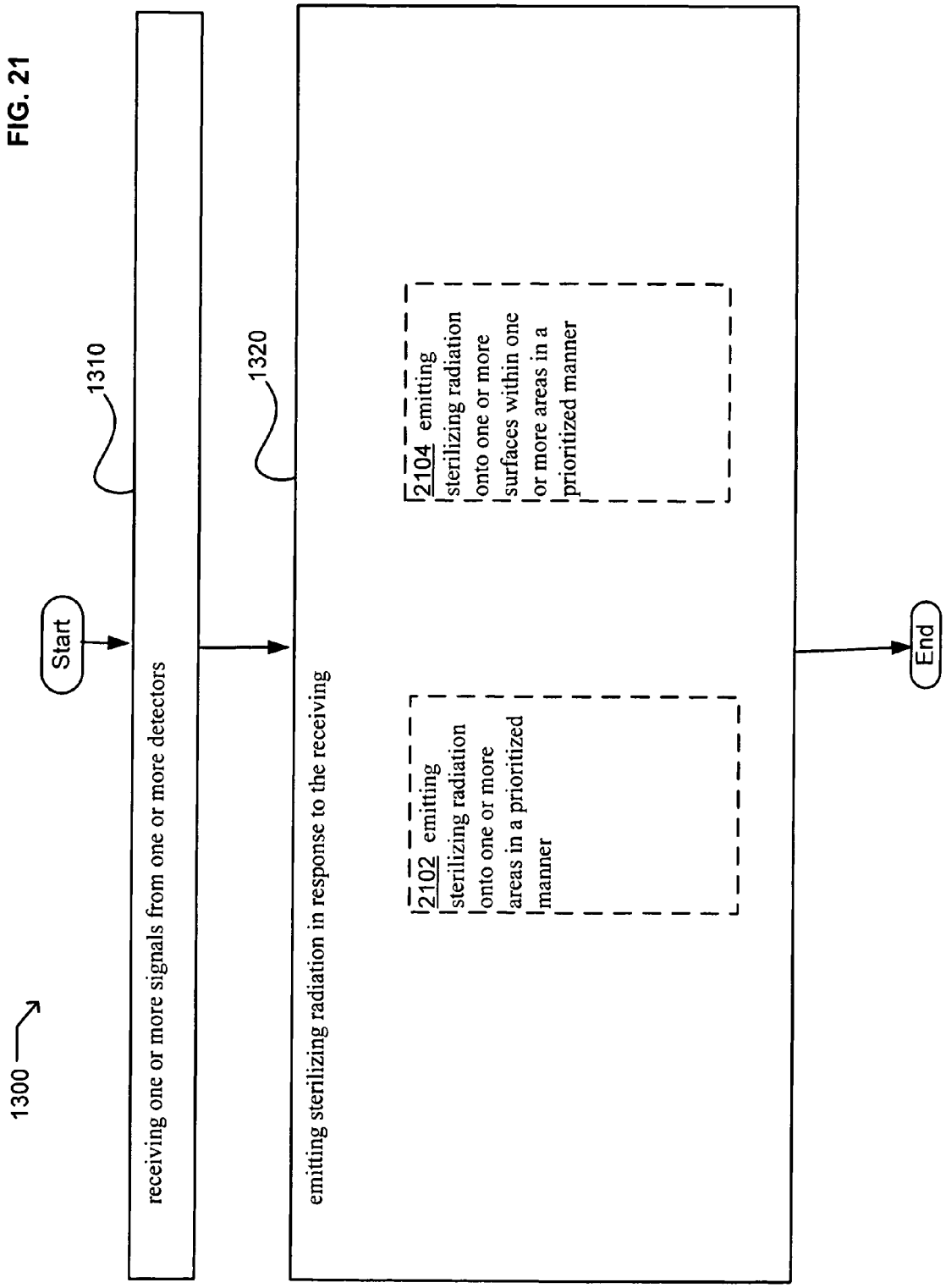
FIG. 21 illustrates an alternative embodiment of the example operation flow of FIG. 13.

FIG. 21 illustrates alternative embodiments of the example operational flow 1300 of FIG. 13. FIG. 21 illustrates example embodiments where the emitting operation 1320 may include at least one additional operation. Additional operations may include an operation 2102, and/or an operation 2104.

At operation 2102, the emitting operation 1320 may include emitting sterilizing radiation onto one or more areas in a prioritized manner. In some embodiments, one or more sources of sterilizing radiation emit sterilizing radiation in response to one or more receiving units. In some embodiments, one or more sources of sterilizing radiation emit sterilizing radiation onto one or more areas in a prioritized manner. In some embodiments, a prioritized manner includes irradiating one or more areas with respect to immediacy, latency, intensity, and the like. In some embodiments, a prioritized manner includes irradiating one or more areas with regard to time-integrated intensity of sterilizing radiation such as irradiation of one or more areas as functions of either relative or absolute locations in the reference enclosed volume so that high-patient-hazard or high-infectivity-likelihood areas and volumes can be specified for the most rigorous and/or frequent irradiation.

At operation 2102, the emitting operation 1320 may include emitting sterilizing radiation onto one or more surfaces within one or more areas in a prioritized manner. In some embodiments, one or more sources of sterilizing radiation emit sterilizing radiation in response to one or more receiving units. In some embodiments, one or more sources of sterilizing radiation emit sterilizing radiation onto one or more surfaces within one or more areas in a prioritized manner. In some embodiments, a prioritized manner includes irradiating one or more surfaces with respect to immediacy, latency, intensity, and the like. In some embodiments, a prioritized manner includes irradiating one or more surfaces with regard to time-integrated intensity of sterilizing radiation such as irradiation of one or more surfaces as functions of either relative or absolute locations in the reference enclosed volume so that high-patient-hazard or high-infectivity-likelihood surfaces and volumes can be specified for the most rigorous and/or frequent irradiation.

Figure 22:
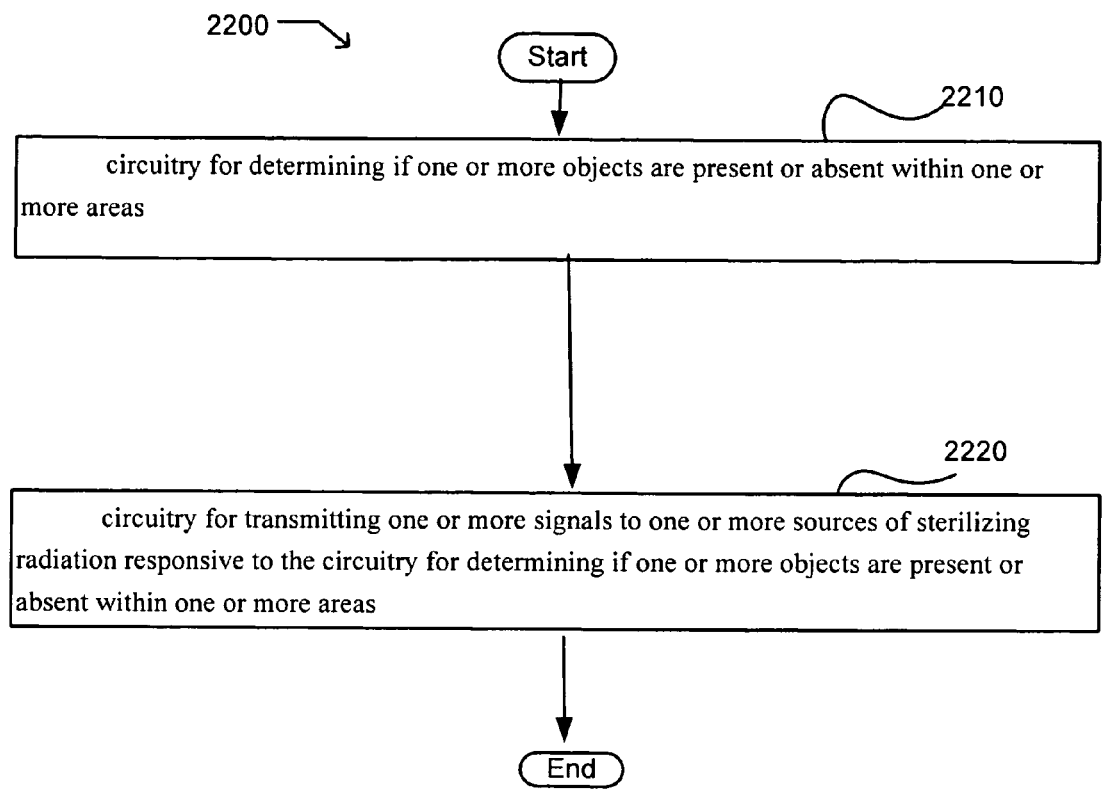
FIG. 22 illustrates an operational flow representing example operations related to sterilization systems.

FIG. 22 illustrates an operational flow 2200 representing examples of operations that are related to the performance of a sterilization method. In FIG. 22 and in following figures that include various examples of operations used during performance of the sterilization method, discussion and explanation may be provided with respect to the above-described example of FIG. 1D, and/or with respect to other examples and contexts. However, it should be understood that the operations may be executed in a number of other environments and contexts, and/or modified versions of FIG. 1D. Also, although the various operations are presented in the sequence(s) illustrated, it should be understood that the various operations may be performed in other orders than those which are illustrated, or may be performed concurrently.

After a start operation, the operational flow 2200 includes an operation 2210 involving circuitry for determining if one or more objects are present or absent within one or more areas. In some embodiments, the circuitry for determining may be used to determine if one or more objects are present within one or more areas. In some embodiments, the circuitry for determining is used to determine the presence or absence of one or more objects within one area. In some embodiments, the circuitry for determining is used to determine the presence or absence of one or more objects within two or more areas.

The operational flow 2200 also includes an operation 2220 involving circuitry for transmitting one or more signals to one or more sources of sterilizing radiation responsive to the circuitry for determining if one or more objects are present or absent within one or more areas. In some embodiments, the circuitry for transmitting can transmit one or more signals to a single source of sterilizing radiation or to numerous sources of sterilizing radiation. For example, in some embodiments, the circuitry for transmitting can transmit one signal to one source of sterilizing radiation. In some embodiments, the circuitry for transmitting can transmit more than one signal to one source of sterilizing radiation. In other embodiments, the circuitry for transmitting can transmit one signal to more than one source of sterilizing radiation. In still other embodiments, the circuitry for transmitting can transmit more than one signal to more than one source of sterilizing radiation.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents). In addition, user 118, as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

What is claimed is:

1. A sterilization method comprising:
   determining if one or more objects are absent from one or more areas; and
   transmitting one or more signals to one or more sources of sterilizing radiation to instruct the one or more sources of sterilizing radiation to emit sterilizing radiation in response to the determining, wherein the transmitting one or more signals to one or more sources of sterilizing radiation to instruct the one or more sources of sterilizing radiation to emit sterilizing radiation in response to the determining includes:
       transmitting the one or more signals to the one or more sources of sterilizing radiation in response to determining one or more distances between one or more surfaces within the one or more areas.

2. The method of claim 1, wherein the determining if one or more objects are absent from one or more areas comprises:
   detecting one or more signals associated with one or more humans.

3. The method of claim 1, wherein the determining if one or more objects are absent from one or more areas comprises:
   determining if one or more shadows are present within the one or more areas.

4. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation as ultraviolet light.

5. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation onto the one or more objects.

6. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation onto the one or more areas according to one or more sterilization levels assigned to the one or more areas.

7. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation substantially constantly.

8. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation as a pulse.

9. The method of claim 1, wherein the transmitting the one or more signals to the one or more sources of sterilizing radiation in response to determining one or more distances between one or more surfaces within the one or more areas comprises:
   transmitting the one or more signals to the one or more sources of sterilizing radiation to instruct the one or more sources of sterilizing radiation to emit sterilizing radiation as ultraviolet light having a wavelength between 100 and 400 nanometers.

10. The method of claim 1, wherein the transmitting the one or more signals to the one or more sources of sterilizing radiation in response to determining one or more distances between one or more surfaces within the one or more areas comprises:
    transmitting the one or more signals to the one or more sources of sterilizing radiation to instruct the one or more sources of sterilizing radiation to direct sterilizing radiation emitted from the one or more sources of sterilizing radiation.

11. The method of claim 1, wherein the transmitting the one or more signals to the one or more sources of sterilizing radiation in response to determining one or more distances between one or more surfaces within the one or more areas comprises:
    transmitting the one or more signals to the one or more sources of sterilizing radiation to instruct the one or more sources of sterilizing radiation to avoid emitting sterilizing radiation onto the one or more objects.

12. The method of claim 1, wherein the transmitting the one or more signals to the one or more sources of sterilizing radiation in response to determining one or more distances between one or more surfaces within the one or more areas comprises:
    transmitting the one or more signals to the one or more sources of sterilizing radiation to instruct the one or more sources of sterilizing radiation to emit sterilizing radiation onto the one or more areas in a prioritized manner.

* * * * *